US006982251B2

(12) United States Patent
Ghosal et al.

(10) Patent No.: US 6,982,251 B2
(45) Date of Patent: Jan. 3, 2006

(54) SUBSTITUTED 2-AZETIDINONES USEFUL AS HYPOCHOLESTEROLEMIC AGENTS

(75) Inventors: Anima Ghosal, Edison, NJ (US); Shmuel Zbaida, East Brunswick, NJ (US); Swapan K. Chowdhury, Warren, NJ (US); Robert M. Iannucci, Hampton, NJ (US); Wenqing Feng, Chatham, NJ (US); Kevin B. Alton, Cedar Knolls, NJ (US); James E. Patrick, Belle Mead, NJ (US); Harry R. Davis, Berkeley Heights, NJ (US)

(73) Assignee: Schering Corporation, Kenilworth, NJ (US)

( * ) Notice: Subject to any disclaimer, the term of this patent is extended or adjusted under 35 U.S.C. 154(b) by 205 days.

(21) Appl. No.: 10/166,942

(22) Filed: Jun. 11, 2002

(65) Prior Publication Data

US 2003/0105028 A1 Jun. 5, 2003

Related U.S. Application Data

(63) Continuation-in-part of application No. 10/023,295, filed on Dec. 17, 2001, now abandoned.
(60) Provisional application No. 60/256,875, filed on Dec. 20, 2000.

(51) Int. Cl.
*A61K 31/7056* (2006.01)
*A61K 31/397* (2006.01)
*A61K 31/675* (2006.01)
*C07H 17/02* (2006.01)
*C07D 25/08* (2006.01)

(52) U.S. Cl. ............... 514/23; 514/79; 514/210.02; 536/17.4; 540/200
(58) Field of Classification Search ............ 514/23, 514/79, 210.02, 200; 536/17.4; 540/200

See application file for complete search history.

(56) References Cited

U.S. PATENT DOCUMENTS

| | | | |
|---|---|---|---|
| 2,809,194 A | 10/1957 | Novello | |
| 3,108,097 A | 10/1963 | Ugi | |
| 3,152,173 A | 10/1964 | Ehrhart | |
| 3,267,104 A | 8/1966 | Hermans | |
| 3,399,192 A | 8/1968 | Regnier | |
| 3,692,895 A | 9/1972 | Nelson | |
| 3,716,583 A | 2/1973 | Nakamura | |
| 3,781,328 A | 12/1973 | Witte | |
| 3,948,973 A | 4/1976 | Phillips | |
| 4,072,705 A | 2/1978 | Mieville | |
| 4,075,000 A | 2/1978 | Abdulla | |
| 4,144,232 A | 3/1979 | Koppel | |
| 4,148,923 A | 4/1979 | Giudicelli | |
| 4,166,907 A | 9/1979 | Krapcho | |

(Continued)

FOREIGN PATENT DOCUMENTS

| | | | |
|---|---|---|---|
| BE | 884722 A | 12/1980 | |
| CA | 2253769 | 11/1999 | |
| DE | 2046823 A | 3/1972 | |
| DE | 2521113 A | 3/1976 | |
| EP | 0002151 B1 | 5/1979 | |
| EP | 0002151 A1 | 5/1979 | |
| EP | 0010299 B1 | 2/1984 | |
| EP | 0179559 A2 | 4/1986 | |
| EP | 0199630 A1 | 10/1986 | |
| EP | 0264231 A1 | 4/1988 | |
| EP | 0266896 B1 | 5/1988 | |
| EP | 0274873 B1 | 7/1988 | |
| EP | 0288973 B1 | 11/1988 | |
| EP | 0311366 B1 | 4/1989 | |

(Continued)

OTHER PUBLICATIONS

Wu et al, J. Org. Chem. 1999, 64, 3714–3718.*
Vaccaro et al, Bioorganic and Medicinal Chemistry Letters, 1998, 8, 313–318.*
Wu et al "A novel One–Step Diastereo– and Enantioselective Formation of trans–Azetidinones and Its Application to the Total Synthesis of Cholesterol Absorption Inhibitors", Journal of Organic Chemistry 1999, 64, 3714–3718.*
*Exhibit A:* SCH 58235 Micronized (ezetimibe), Drug Formulation Development Summary.
*Exhibit B:* SCH 58235 (ezetimibe), Drug Formulation Development Summary.
*Exhibit C:* SCH 58235 (ezetimibe), Drug Formulation Development Summary.
*Exhibit D:* SCH 58235 (ezetimibe), Drug Formulation Development Summary.
*Exhibit E:* SCH 58235 (ezetimibe), Drug Formulation Development Summary.

(Continued)

*Primary Examiner*—James O. Wilson
*Assistant Examiner*—Ganapathy Krishnan
(74) *Attorney, Agent, or Firm*—Richard A. Elder

(57) ABSTRACT

Hypocholesterolemic substituted 2-azetidinone compounds of the formula:

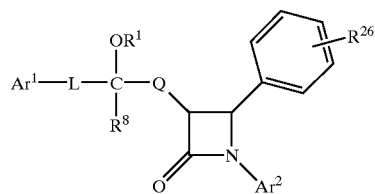

are disclosed, as well as a methods of lowering cholesterol by administering said compounds, pharmaceutical compositions containing them, and the combination of a substituted 2-azetidinone cholesterol-lowering agent and a cholesterol biosynthesis inhibitor for the treatment and prevention of atherosclerosis.

27 Claims, No Drawings

U.S. PATENT DOCUMENTS

| | | |
|---|---|---|
| 4,178,695 A | 12/1979 | Erbeia |
| 4,179,515 A | 12/1979 | Mieville |
| 4,235,896 A | 11/1980 | Mieville |
| 4,239,763 A | 12/1980 | Milavec |
| 4,250,191 A | 2/1981 | Edwards |
| 4,260,743 A | 4/1981 | Bose |
| 4,304,718 A | 12/1981 | Kamiya |
| 4,375,475 A | 3/1983 | Willard |
| 4,443,372 A | 4/1984 | Luo |
| 4,444,784 A | 4/1984 | Hoffman |
| 4,472,309 A | 9/1984 | Kamiya |
| 4,479,900 A | 10/1984 | Luo |
| 4,500,456 A | 2/1985 | Spitzer |
| 4,534,786 A | 8/1985 | Luo |
| 4,564,609 A | 1/1986 | Tamura |
| 4,567,195 A | 1/1986 | Schwarz |
| 4,576,748 A | 3/1986 | Greenlee |
| 4,576,749 A | 3/1986 | Zahler |
| 4,576,753 A | 3/1986 | Kamiya |
| 4,581,170 A | 4/1986 | Mueller |
| 4,595,532 A | 6/1986 | Miller |
| 4,602,003 A | 7/1986 | Malinow |
| 4,602,005 A | 7/1986 | Malinow |
| 4,614,614 A | 9/1986 | Ernest |
| 4,616,047 A | 10/1986 | Lafon |
| 4,620,867 A | 11/1986 | Luo |
| 4,626,549 A | 12/1986 | Molloy |
| 4,633,017 A | 12/1986 | Mueller |
| 4,642,903 A | 2/1987 | Davies |
| 4,654,362 A | 3/1987 | Lommen |
| 4,675,399 A | 6/1987 | Miller |
| 4,680,289 A | 7/1987 | Applezweig |
| 4,680,391 A | 7/1987 | Firestone |
| 4,687,777 A * | 8/1987 | Meguro et al. ............ 514/342 |
| 4,739,101 A | 4/1988 | Bourgogne |
| 4,778,883 A | 10/1988 | Yoshioka |
| 4,784,734 A | 11/1988 | Torii |
| 4,794,108 A | 12/1988 | Kishimoto |
| 4,800,079 A | 1/1989 | Boyer |
| 4,803,266 A | 2/1989 | Kawashima |
| 4,814,354 A | 3/1989 | Ghebre-Sellassie |
| 4,834,846 A | 5/1989 | Abramson |
| 4,871,752 A | 10/1989 | Ilg et al. |
| 4,876,365 A | 10/1989 | Kirkup |
| 4,879,301 A | 11/1989 | Umio |
| 4,895,726 A | 1/1990 | Curtet |
| 4,925,672 A | 5/1990 | Gremm |
| 4,937,267 A | 6/1990 | Holloway |
| 4,939,248 A | 7/1990 | Yoshioka |
| 5,021,461 A | 6/1991 | Robinson et al. |
| 5,093,365 A | 3/1992 | Berge |
| 5,106,833 A | 4/1992 | Broze |
| 5,110,730 A | 5/1992 | Edgington |
| 5,120,713 A | 6/1992 | Mugica |
| 5,278,176 A | 1/1994 | Lin |
| 5,358,852 A | 10/1994 | Wu |
| 5,385,885 A | 1/1995 | Gasic |
| 5,567,439 A | 10/1996 | Myers |
| 5,576,014 A | 11/1996 | Mizumoto |
| 5,587,172 A | 12/1996 | Cherukuri |
| 5,587,180 A | 12/1996 | Allen, Jr. |
| 5,591,456 A | 1/1997 | Franson |
| 5,593,971 A | 1/1997 | Tschollar |
| 5,595,761 A | 1/1997 | Allen, Jr. |
| 5,607,697 A | 3/1997 | Alkire |
| 5,612,353 A | 3/1997 | Ewing |
| 5,612,367 A | 3/1997 | Timko |
| 5,612,378 A | 3/1997 | Tianbao |
| 5,618,707 A | 4/1997 | Homann |
| 5,622,719 A | 4/1997 | Myers |
| 5,622,985 A | 4/1997 | Olukotun |
| 5,624,920 A | 4/1997 | McKittrick |
| 5,627,176 A | 5/1997 | Kirkup |
| 5,631,023 A | 5/1997 | Kearney |
| 5,631,365 A * | 5/1997 | Rosenblum et al. ........ 540/200 |
| 5,633,246 A | 5/1997 | McKittrick |
| 5,635,210 A | 6/1997 | Allen, Jr. |
| 5,639,475 A | 6/1997 | Bettman |
| 5,639,739 A | 6/1997 | Dominguez |
| 5,656,624 A | 8/1997 | Vaccaro |
| 5,661,145 A | 8/1997 | Davis |
| 5,674,893 A | 10/1997 | Behounek |
| 5,688,785 A | 11/1997 | Vaccaro |
| 5,688,787 A | 11/1997 | Burnett |
| 5,688,990 A | 11/1997 | Shankar |
| 5,691,375 A | 11/1997 | Behounek |
| 5,698,527 A | 12/1997 | Kim |
| 5,698,548 A | 12/1997 | Dugar |
| 5,703,188 A | 12/1997 | Mandeville |
| 5,703,234 A | 12/1997 | Iwasaki et al. |
| 5,709,886 A | 1/1998 | Bettman |
| 5,718,388 A | 2/1998 | Czekai |
| 5,728,827 A | 3/1998 | Thiruvengadam et al. |
| 5,734,077 A | 3/1998 | Regnier |
| 5,739,321 A | 4/1998 | Wu |
| 5,744,467 A | 4/1998 | McKittrick |
| 5,747,001 A | 5/1998 | Wiedmann |
| 5,753,254 A | 5/1998 | Khan |
| 5,756,470 A | 5/1998 | Yumibe |
| 5,759,865 A | 6/1998 | Bruns |
| 5,767,115 A | 6/1998 | Rosenblum |
| 5,776,491 A | 7/1998 | Allen |
| 5,807,576 A | 9/1998 | Allen |
| 5,807,577 A | 9/1998 | Ouali |
| 5,807,578 A | 9/1998 | Acosta-Cuello |
| 5,807,834 A | 9/1998 | Morehouse |
| 5,808,056 A | 9/1998 | Amato |
| 5,817,806 A | 10/1998 | Rossi |
| 5,994,554 A | 11/1999 | Kliewer |
| 6,008,237 A | 12/1999 | Sahoo |
| 6,028,109 A | 2/2000 | Willson |
| 6,030,990 A | 2/2000 | Maeda et al. |
| 6,033,656 A | 3/2000 | Mikami |
| 6,040,147 A | 3/2000 | Ridker |
| 6,121,319 A | 9/2000 | Somers |
| 6,127,424 A | 10/2000 | Martin |
| 6,140,354 A | 10/2000 | Dax |
| 6,147,090 A | 11/2000 | DeNinno |
| 6,147,109 A | 11/2000 | Liao |
| 6,147,250 A | 11/2000 | Somers |
| 6,159,997 A | 12/2000 | Tsujita |
| 6,162,805 A | 12/2000 | Hefti |
| 6,166,049 A | 12/2000 | Smith et al. |
| 6,174,665 B1 | 1/2001 | Dullien |
| 6,180,138 B1 | 1/2001 | Engh |
| 6,180,625 B1 | 1/2001 | Persson |
| 6,180,660 B1 | 1/2001 | Whitney |
| 6,191,117 B1 | 2/2001 | Kozachuk |
| 6,191,159 B1 | 2/2001 | Pinto |
| 6,200,998 B1 | 3/2001 | Sahoo |
| 6,207,697 B1 | 3/2001 | Han |
| 6,207,699 B1 | 3/2001 | Rothman |
| 6,207,822 B1 | 3/2001 | Thiruvengadam |
| 6,214,831 B1 | 4/2001 | Yokoo |
| 6,235,706 B1 | 5/2001 | Gould |
| 6,245,743 B1 | 6/2001 | Marlowe |
| 6,248,781 B1 | 6/2001 | Jeppesen |
| 6,251,852 B1 | 6/2001 | Gould |
| 2001/0028895 A1 | 10/2001 | Bisgaier |
| 2002/0006919 A1 | 1/2002 | Thosar |
| 2002/0039774 A1 | 4/2002 | Kramer et al. |

| | | | | | | |
|---|---|---|---|---|---|---|
| 2002/0128252 A1 | 9/2002 | Glombik et al. | | WO | WO 95/08532 | 3/1995 |
| 2002/0128253 A1 | 9/2002 | Glombik et al. | | WO | WO 95/18143 | 7/1995 |
| 2002/0132855 A1 | 9/2002 | Nelson et al. | | WO | WO 95/26334 | 10/1995 |
| 2002/0137689 A1 | 9/2002 | Glombik et al. | | WO | WO 95/28919 | 11/1995 |
| 2003/0153541 A1 | 8/2003 | Dudley et al. | | WO | WO 95/35277 | 12/1995 |
| | | | | WO | WO 96/00288 | 1/1996 |
| FOREIGN PATENT DOCUMENTS | | | | WO | WO 96/09827 | 4/1996 |
| EP | 0333268 A1 | 9/1989 | | WO | WO 96/16037 | 5/1996 |
| EP | 0337549 A1 | 10/1989 | | WO | WO 96/19450 | 6/1996 |
| EP | 0365364 A2 | 4/1990 | | WO | WO 96/19987 | 7/1996 |
| EP | 0369686 A1 | 5/1990 | | WO | WO 96/40255 | 12/1996 |
| EP | 0375527 A1 | 6/1990 | | WO | EP 0 753 298 A | 1/1997 |
| EP | 0199630 B1 | 9/1990 | | WO | WO 97/16455 | 5/1997 |
| EP | 0401705 A3 | 12/1990 | | WO | WO 97/18304 | 5/1997 |
| EP | 0415487 A2 | 3/1991 | | WO | WO 97/21676 | 6/1997 |
| EP | 0455042 A1 | 11/1991 | | WO | WO 97/25042 | 7/1997 |
| EP | 0457514 A1 | 11/1991 | | WO | WO 97/28149 | 8/1997 |
| EP | 0461548 A3 | 12/1991 | | WO | WO 97/31907 | 9/1997 |
| EP | 0462667 A2 | 12/1991 | | WO | WO 97/35576 | 10/1997 |
| EP | 0475148 A1 | 3/1992 | | WO | WO 97/41098 | 11/1997 |
| EP | 0475755 B1 | 3/1992 | | WO | WO 97/46238 | 12/1997 |
| EP | 0481671 A1 | 4/1992 | | WO | WO 98/01100 | 1/1998 |
| EP | 0482498 A3 | 4/1992 | | WO | WO 98/05331 | 2/1998 |
| EP | 0524595 A1 | 1/1993 | | WO | WO 98/14179 | 4/1998 |
| EP | 0337549 B1 | 10/1995 | | WO | WO 98/31360 | 7/1998 |
| EP | 0720599 B1 | 7/1996 | | WO | WO 98/31361 | 7/1998 |
| EP | 0457514 B1 | 8/1996 | | WO | WO 98/31366 | 7/1998 |
| EP | 0793958 A2 | 9/1997 | | WO | WO 98/43081 | 10/1998 |
| EP | 0814080 A1 | 12/1997 | | WO | WO 98/46215 | 10/1998 |
| EP | 0904781 A2 | 3/1999 | | WO | WO 98/47518 | 10/1998 |
| EP | 1 036 563 | 9/2000 | | WO | WO 98/57652 | 12/1998 |
| EP | 1048295 A2 | 11/2000 | | WO | WO 99/06035 | 2/1999 |
| FR | 1103113 | 10/1955 | | WO | WO 99/06046 | 2/1999 |
| FR | 2779347 | 12/1997 | | WO | WO 99/08501 | 2/1999 |
| GB | 861367 | 2/1961 | | WO | WO 99/22728 | 2/1999 |
| GB | 902658 | 8/1962 | | WO | WO 99/09967 | 3/1999 |
| GB | 1415295 | 11/1975 | | WO | WO 99/11260 | 3/1999 |
| GB | 2329334 A | 3/1999 | | WO | WO 99/12534 | 3/1999 |
| JP | 136485 | 5/1981 | | WO | WO 99/04815 | 4/1999 |
| JP | 028057 | 10/1981 | | WO | WO 99/15159 | 4/1999 |
| JP | 180212 | 3/1986 | | WO | WO 99/15520 | 4/1999 |
| JP | 121479 | 12/1986 | | WO | WO 99/18072 | 4/1999 |
| JP | 61280295 A | 12/1986 | | WO | WO 99/20275 | 4/1999 |
| JP | 219681 | 4/1987 | | WO | WO 99/20614 | 4/1999 |
| JP | 63017859 A | 1/1988 | | WO | WO 99/29300 | 6/1999 |
| JP | 91068020 | 10/1991 | | WO | WO 99/38498 | 8/1999 |
| JP | 4054182 A | 2/1992 | | WO | WO 99/38845 | 8/1999 |
| JP | 4266869 A | 9/1992 | | WO | WO 99/38850 | 8/1999 |
| JP | 4356195 A | 12/1992 | | WO | WO 99/46232 | 9/1999 |
| JP | 4356495 | 12/1992 | | WO | WO 99/47123 | 9/1999 |
| JP | 5058993 A | 3/1993 | | WO | WO 99/48488 | 9/1999 |
| JP | 5194209 | 8/1993 | | WO | WO 99/66929 | 12/1999 |
| JP | 5239020 A | 9/1993 | | WO | WO 99/66930 | 12/1999 |
| JP | 94047573 | 6/1994 | | WO | WO 00/04011 | 1/2000 |
| JP | 95051558 B2 | 6/1995 | | WO | WO 00/07617 | 2/2000 |
| WO | WO 82/01649 | 5/1982 | | WO | WO 00/16749 | 3/2000 |
| WO | WO 87/04429 | 7/1987 | | WO | WO 00/18395 | 4/2000 |
| WO | WO 88/04656 | 6/1988 | | WO | WO 00/20623 | 4/2000 |
| WO | WO 88/05296 | 7/1988 | | WO | WO 00/23415 | 4/2000 |
| WO | WO 91/03249 | 3/1991 | | WO | WO 00/23416 | 4/2000 |
| WO | WO 92/13837 | 8/1992 | | WO | WO 00/23425 | 4/2000 |
| WO | WO 93/02048 | 2/1993 | | WO | WO 00/23445 | 4/2000 |
| WO | WO 93/07167 | 4/1993 | | WO | WO 00/23451 | 4/2000 |
| WO | WO 93/11150 | 6/1993 | | WO | WO 00/28981 | 5/2000 |
| WO | WO 94/00480 | 1/1994 | | WO | WO 00/31548 | 6/2000 |
| WO | WO 94/14433 | 7/1994 | | WO | WO 00/32189 | 6/2000 |
| WO | WO 94/17038 | 8/1994 | | WO | WO 00/34240 | 6/2000 |
| WO | WO 94/20535 | 9/1994 | | WO | WO 00/37057 | 6/2000 |
| WO | WO 94/26738 | 11/1994 | | WO | WO 00/37078 | 6/2000 |
| WO | WO 95/04533 | 2/1995 | | WO | WO 00/38721 | 7/2000 |
| WO | WO 95/06470 | 3/1995 | | WO | WO 00/38722 | 7/2000 |

| | | |
|---|---|---|
| WO | WO 00/38723 | 7/2000 |
| WO | WO 00/38724 | 7/2000 |
| WO | WO 00/38725 | 7/2000 |
| WO | WO 00/38726 | 7/2000 |
| WO | WO 00/38727 | 7/2000 |
| WO | WO 00/38728 | 7/2000 |
| WO | WO 00/38729 | 7/2000 |
| WO | WO 00/40247 | 7/2000 |
| WO | WO 00/45817 | 8/2000 |
| WO | WO 00/50392 | 8/2000 |
| WO | WO 00/53149 | 9/2000 |
| WO | WO 00/53173 | 9/2000 |
| WO | WO 00/53563 | 9/2000 |
| WO | WO 00/56403 | 9/2000 |
| WO | WO 00/57859 | 10/2000 |
| WO | WO 00/57918 | 10/2000 |
| WO | WO 00/60107 | 10/2000 |
| WO | WO 00/63153 | 10/2000 |
| WO | WO 00/63161 | 10/2000 |
| WO | WO 00/63190 | 10/2000 |
| WO | WO 00/63196 | 10/2000 |
| WO | WO 00/63209 | 10/2000 |
| WO | WO 00/63703 | 10/2000 |
| WO | WO 00/69412 | 11/2000 |
| WO | WO 00/69445 | 11/2000 |
| WO | WO 00/72825 | 12/2000 |
| WO | WO 00/72829 | 12/2000 |
| WO | WO 00/75103 | 12/2000 |
| WO | WO 00/76482 | 12/2000 |
| WO | WO 00/76488 | 12/2000 |
| WO | WO 00/78312 | 12/2000 |
| WO | WO 00/78313 | 12/2000 |
| WO | WO 01/00579 | 1/2001 |
| WO | WO 01/00603 | 1/2001 |
| WO | WO 01/08686 | 2/2001 |
| WO | WO 01/12176 | 2/2001 |
| WO | WO 01/12187 | 2/2001 |
| WO | WO 01/12612 | 2/2001 |
| WO | WO 01/14349 | 3/2001 |
| WO | WO 01/14350 | 3/2001 |
| WO | WO 01/14351 | 3/2001 |
| WO | WO 01/15744 | 3/2001 |
| WO | WO 01/16120 | 3/2001 |
| WO | WO 01/17994 | 3/2001 |
| WO | WO 01/18210 | 3/2001 |
| WO | WO 01/21181 | 3/2001 |
| WO | WO 01/21259 | 3/2001 |
| WO | WO 01/21578 | 3/2001 |
| WO | WO 01/21647 | 3/2001 |
| WO | WO 01/22962 | 4/2001 |
| WO | WO 01/25225 | 4/2001 |
| WO | WO 01/25226 | 4/2001 |
| WO | WO 01/30343 | 5/2001 |
| WO | WO 01/32161 | 5/2001 |
| WO | WO 01/34148 | 5/2001 |
| WO | WO 01/35970 | 5/2001 |
| WO | WO 01/40192 | 6/2001 |
| WO | WO 01/45676 | 6/2001 |
| WO | WO 01/49267 | 7/2001 |
| WO | WO 01/60807 | 8/2001 |
| WO | WO 02/058731 | 8/2001 |
| WO | WO 01/64221 | 9/2001 |
| WO | WO 01/76632 | 10/2001 |
| WO | WO 01/96347 | 12/2001 |
| WO | WO 02/08188 | 1/2002 |
| WO | WO 02/26729 | 4/2002 |
| WO | WO 02/50027 | 6/2002 |
| WO | WO 02/50060 | 6/2002 |
| WO | WO 02/50068 | 6/2002 |
| WO | WO 02/50090 | 6/2002 |
| WO | WO 02/058685 | 8/2002 |
| WO | WO 02/058696 | 8/2002 |
| WO | WO 02/058732 | 8/2002 |
| WO | WO 02/058733 | 8/2002 |
| WO | WO 02/058734 | 8/2002 |
| WO | WO 02/064094 | 8/2002 |
| WO | WO 02/064130 | 8/2002 |
| WO | WO 02/064549 | 8/2002 |
| WO | WO 02/064664 | 8/2002 |
| WO | WO 02/072104 | 9/2002 |
| WO | WO 02/081454 | 10/2002 |
| WO | WO 03/018024 | 3/2003 |
| WO | WO 03/018059 | 3/2003 |
| WO | WO 03/039542 | 5/2003 |
| WO | WO 03/074101 | 9/2003 |
| WO | WO 03/088962 | 10/2003 |

OTHER PUBLICATIONS

*Exhibit F:* SCH 58235 (ezetimibe), Drug Formulation Development Summary.
*Exhibit G:* SCH 58235 (ezetimibe), Drug Formulation Development Summary.
*Exhibit H:* SCH 58235 (ezetimibe), Drug Formulation Development Summary.
*Exhibit 1:* Master Sheet for the SCH 58235 and Lovastatin Research Study, *Schering–Plough Research Institute* (Protocol No. C906–411), p. 1576–1585.
*Exhibit 2:* Medical Research Study #1055/97, SCH 58235: Bioavailability of Single Oral Doses of Two Prototype Tablet Formulations and the Reference Capsule Formulation of SCH 58235 in Normal Male Volunteers: A Four Way Crossover Study #C97–221–01, Informed Consent, *Peninsular Testing Corporation,* p. 106–112.
*Exhibit 3:* Consent Form to Participate in a Research Study, "A Phase II Double Blind Dose Response Investigation of Efficacy and Safety of Four Doses of SCH 58235 Compared to Placebo in Subjects with Primary Hypercholesterolemia," *Schering–Plough Research Institute* (Protocol No. C98–010), p. 1558–1566.
*Exhibit 4:* Medical Research Study #1096/99, SCH 58235: Pharmacokinetic Pharmacodynamic Drug Interaction Study with Digoxin in Healthy Volunteers #C98–114, Informed Consent, *Peninsular Testing Corporation,* p. 124–130.
*Exhibit 5:* Informed Consent, "SCH 58235: Assessment of Multiple–Dose Drug Interaction Between 58235 and Gemfibrozil in Healthy Volunteers," *Schering–Plough Research Institute,* p. 1–8.
PCT International Search Report for Application No. PCT/US01/49127.
Amer. Chem. Soc'y Registry (ACS) Nos. 272778–13–9, 231301–00–1, 215603–90–0, 215603–89–7, 215603–88–6, 208259–78–3, 200260–28–2, 190595–65–4, 190448–81–8, 190448–62–5, 190448–61–4, 190448–56–7, 163380–21–0, 163380–20–9, 163222–40–0 and 163222–39–7 (2000).
Vaccaro et al., Carboxy–Substituted 2–Azetidinone As Cholesterol Absorption Inhibitors, Biorganic & Medicinal Chemistry Letters 8, (1998), pp. 319–322.
Vaccaro et al., Sugar–Substituted 2–Azetidinone Cholesterol Absorption Inhibitors: Enhanced Potency By Modification Of The Sugar, Bioorganic & Medicinal Chemistry Letters 8, (1998), pp 313–318.
Stuart B. Rosenblum et al., Discovery of 1–(4–Fluorophenyl)–(3R)–[3–fluorophenyl)–(3S)–hydroxypropyl]–(4S)–(4–hydroxyphenyl)–2–azetidinone (SCH 58235): A Designed, Potent, Orally Active Inhibitor of Cholesterol Absorption, J. Med. Chem., 973–980, 1998.

Gilbert R. Thompson et al., Novel lipid–regulating drugs, Exp. Opin. Invest. Drugs 9(11):2619–2628, 2000.

T. Kosoglou et al., Coadministration of Ezetimibe and Fenofibrate Leads to Favorable Effects on Apo ClII and LDL Subfractions, Atheroselerosis, 2, p. 89, 2001.

Harry R. Davis et al., The Synergistic Hypocholesterolemic Activity of the Potent Cholesterol Absorption Inhibitor, Ezetimibe, in Combination With 3–Hydroxy–3–Methylglutaryl Coenzyme A Reductase Inhibitors in Dogs, Metabolism, vol. 50, No. 10, pp. 1234–1241, 2001.

Study Showed Ezetimibe Significantly Reducted Levels of LDL Cholesterol or "Bad" Cholesterol in Pateints, Schering Press Release.

T. Kosoglou et al., Pharmacodynamic Interaction Between Fenofibrate and the Cholesterol Absorption Inhibitor Ezetimibe, Atheroselerosis (2):38, 2001.

Remington's Pharmaceutical Sciences, $18^{th}$ ed. 1990 p. 1319, 1633–1647.

Baker S G et al., Treatment of homozygous familial hypercholesterolaemia with probucol, South African Medical Journal, 1982.

R. Milanese et al., Xantomi E Ipercolesterolemia: Prevalenza, Diagnosie Terapia, Chron. Derm.

Sorbera et al., Netoglitazone, *Drugs of the Future*, 2002, 27(2): 132–139.

Michel Farnier, Nouvelles approaches médicamenteuses dans le traitement des dyslipidémies, *MT Endocrinologie*, 2002, 4:252–259.

Berger et al., Physiological and Therapeutic Roles of Peroxisome Proliferator–Activated Receptors, *Diabetes Technology & Therapeutics*, 2002, 4:163–174.

Luis Gruberg, MD, Inflammatory Markers in Acute Coronary Syndromes: C–reactive Protein (CRP) and Chlamydia, American Heart Association Scientific Sessions 2000.

T. Kosoglou et al., "CoAdministration of Simvastatin and Ezetimibe Leads to Significant Reduction in LDL–Cholesterol", Proceedings of $3^{rd}$ International Congress on Coronary, Artery Disease from Prevention to Intervention, Lyon, France p. 71 (2000), XP008027568.

Vaccaro, W.D. et al, "Sugar–substituted 2–azetidinone cholesterol absorption inhibitors: enhanced potency by modification of the sugar" *Bioorganic & Medicinal Chemistry Ltrs.*, Oxford, G.B., 8:313–318 (1998).

Vaccaro, W.D. et al., "Carboxy–substituted 2–azetidinones as cholesterol absorption inhibitors", *Bioorganic & Medicinal Chemistry Ltrs.*, Oxford, G.B., 8:319–322 (1998).

H. Davis et al., "Ezetimibe, a Potent Cholesterol Absorption Inhibitor, Inhibits the Developmentof Aterosclerosis in Apo E Knockout Mice", *Arterioscler, Thromb. Vasc. Biol* 21:2032–2038, (Dec. 2001).

Simova, E., "Aldol–type addition of hydrocinnamic acid esters to benzylideneaniline", *Chemical Abstracts No. 15, 86* (Apr. 11, 1997).

Otto et al., Stereochemistry of dehydration and halogenation fo $\alpha R^*$ and $\alpha S^*$ isomeric 3–($\alpha$–hydroxybanzyl)–1,4 diphenyl=2 azetidinones, *Chemical Abstracts No. 19, 99* (Nov. 7, 1983).

T. Durst et al, "Metallation of N–Substituted β–Lactams. A Method of the Introduction of 3–substituents into β–Lactams" *Canadian Journal of Chemistry*, 50:3196–3201 (1971).

Nobuki, O. et al., "Stereoselective syntheses of b–lactam derivatives by ultrasound promoted Reformatskil reaction" *Chemical Abstracts No. 106, 17* (Apr. 27, 1987).

M. Hoekman, et al., "Synthesis of Homologues of 4,5–Dihydroxy–and 4–Hydroxy–5–oxohexanoic Acid γ–Lactones", *J. Agric. Food Chem.*, 30:920–924 (1982).

H. Otto et al. "Darstellung and Stereochemie von 3–(α–Hydroxybenzyl)–1,4–diphenyl–2–azetidononen", *Liebigs Ann. Chem.* 1152–1161 (1983).

G. George et al., "3–(1'–Hydroxyethyl)–2–Azetidinones From 3–Hydroxybutyrates and N–Arylaldimines" *Tetrahedron Letters*, 26:3903–3906 (1985).

Hart et al. "An Enantioselective Approach to Carbapenem Antibodies: Formal Synthesis of (+)–Thienamycin", 26 *Tetrahedron Letters*, 45:5493–5496 (1985).

Panfil, I. et al. "Synthesis of β–Lactams from α,β–Unsaturated Sugar δ–Lactones" 24 *Heterocycles* 6:1609–1617 (1986).

D. Roger Illingworth, "An Overview of Lipid–Lower Drugs" *Drugs* 36:63–71 (1988).

Joseph L. Witztum, M.D., "Current Approaches to Drug Therapy for the Hyercholesterolemic Patient" *Circulation* 80:1101–1114 (1989).

B. Ram et al. "Potential Hypolipidemic agents:Part V", 29B Indian J. Chem. 1134–37 (1990).

Schnitzer–Polokoff, R. et al., "Effects of Acyl–CoA: Choleseraol O–Acyltransferase Inhibition on Cholesteroal Absorption and Plasma Lipoprotein Composition in Hamsters" Comp. Biochem. Physiol. 99A:665–670 (1991).

Horie, M. et al, "Hypolipidemic effects of NB–598 in dogs" *Atherosclerosis* 88: 183–192 (1991).

Baxter, A., "Squalestatin 1, a Potent Inhibitor of Squalene Synthease, Which Lowers Serum Cholesterol in Vivo", *The Journal of Biological Chemistry* 267:11705–11708 (1992).

Summary Factfile, "Anti–Antherosclerotic Agents" *Current Drugs Ltd.* (1992).

Harwood H. James, "Pharmacologic consequences of cholesterol absorption inhibition: alteration in cholesterol metabolism and reduction in plasma cholesterol concentration induced by the synthetic saponin β–tigogenin cellobioside (CP–88818; tiqueside) 1" *Journal of Lipid Research* 34:377–395 (1993).

Salisbury, B. et al., "Hypocholesterolemic activity of a novel inhibitor of cholesterol absorption, SCH 48461" *Atherosclerosis* 115:45–63 (1995).

Clader, J. W. et al., "Substituted (1,2–Diarylethyl)amide Acyl–CoA;Cholesterol Acyltransferase Inhibitors: Effect of Polar Groups in Vitro and in Viro Activity" *Journal of Medicinal Chemistry* 38:1600–1607 (1995).

Sybertz, E., "Sch 48461, a novel inhibitor of cholesterol absorption" Atherosclerosis pp. 311–315 (1995).

Vaccaro, W, et al, "2–Azetidinone Cholesterol Absorption Inhibitors: Increased Potency by Substitution of the C–4 Phenyl Ring", *Bioorg. & Med. Chem.* 6:1429–1437 (1998).

G. Wu et al, A Novel One–Step Diastereo–and enantioselective formation of trans–azetidinones and its application to the total synthesis of cholesterol absorption inhibitors A.C.S. (Apr. 21, 1999).

B. Staels, "New Roles for PPARS in Cholesterol Homeostasis", *Trends in Pharmacological Sciences*, 22:9 p. 444 (Sep. 2001).

Abbott et al, "Tricor® Capsules, Micronized", *Physicians Desk Reference*, Jan. 8, 2001.

M. Feher et al., 1991, Lipids and Lipid Disorders, p. 1–87 (1991).

M. Ricote et al., "New Roles for PPARs in Cholesterol Homeostakis", *Trends in Pharmacological Science,* vol. 22, No. 9 441–443 (2001).

C. Dujovne et al, "Reduction of LDL Cholesteral in Patients with Primary Hypercholesterolemia by SCH 48461: Results of a mutlicenter Dose–Ranging Study", *J. Clin,. Pharm.* 41:1 70–78 (Jan. 2001).

W. Oppolzer et al., "Asymmetric Diels—Alder Reactions, Facile Preparation and Structure of Sulfonamido—Isobornyl Acrylates", *Tetrahedron Letters, No. 51,* 25:5885–5888 (1984).

M. Davidson et al., "Colesevelam Hydischolride: a non–absorbed, polymeric cholesterol lowing agent", *Expert Opinion Investigating Drugs,* 11:2663–71, (Nov. 2000).

M. Davidson et al., "Colesevelam hydrochloride (cholestagel): a new, potent bileacid sequestrant associated with a low incidence of gastrointestinal effects", 159 *Arch. Intern. Med.* 16 1893–900 (Sep. 1999).

I. Wester, "Cholesterol—Lowering effect of plant sterols", *Eur. J.Lipid, Sci. Tech.* 37–44 (2000).

A. Andersson et al., "Cholesterol –lowering effects of a stanol ester–containing low fat margarine used in conjunction with a strict lipid–lowing diet", *1 European Heart. J. Supplements* S80–S90 (1999).

H. Gylling et al, Reduction of Serum Cholesterol in Postmenopausal Women with Previous Myocardial Infarction and Cholesterol Malabsorption induced by Dietary Sitostarol Ester Margarine, *96 Circulation124226–4231* (Dec. 16, 1997).

T. Miettinen et al, "Reduction of Serum Cholesterol with Sitostanol–Ester Margarine in a Mildly Hypercholesterolemic Population", *New England Journal of Med.* 333 1308–1312 (Nov. 16, 1995).

T. Bocan et al., "The ACAT Inhibitor Avasimibe Reduces Macrophages and Matrix Metalloproteinase Expression in Atherosclerotic Lesions of Hypercholesterolemic Rabbits", *Arterioscler Thromb Vasc. Biol.* 70–79 (Jan. 2000).

M. Van Heek et al., "In Vivo Metabolism—Based Discovery of a Potent Cholesterol Absorption Inhibitor, SCH 58235, in the Rat and Rhesus Monkey through the indentification of the active metabolites of SCH48461," *283 J. Pharma and Experimental Therapeutics 1* 157–163 (1997).

H. Davis et al. "The Cholesterol Absorption Inhibitor Ezetimible Inhibits the Development of Atherosclerosis in apo E knockout (–/–) mice fed low fat and western diets," *Atherosclerosis 1:*133 (Jul. 2000).

L. Nguyen et al., "Unexpected Failure of Bile Acid Malabsorption to Stimulate Cholesterol Synthesis in Sitosterolemia with Xanthomatosis", *10 Atherosclerosis 2,* 289–297 (1990).

L. Nguyen et al., "Regulation of Cholesterol Biosynthesisin Sitosterolemia: effects of lovastatin, Cholestyramine, and dietary sterol restriction," *32 J.Lipid Res.* 1941–1948 (1991).

M. Cobb et al., "Sitosterolemia: Opposing Effects of cholestryamine and Lovastatin on Plasma Sterol Levels in a Homozygous Girl and Her Heterozygous Father," *45 Metabolism 6* 673–679 (Jun. 1996).

M. Huettinger et al., "Hypolipidemic Activity of HOE–402 is mediated by Stimulation of the LDL Receptor Pathway", *13 Arteriosclerosis and Thrombosis 7* 1005–1012 (Jul. 1993).

J. Best et al., "Diabetic Dyslipidaemia", *59 Drugs 5* 1101–1111 (May 2000).

P. Chong, et al, "Current, New and Future Treatment in Dyslipidaemia and Atherosclerosis", *60 Drugs 1* 55–93 (Jul. 2000).

M. Brown et al, "A Receptor—Mediated Pathway for Cholesterol Homeostasis", *232 Science* 34–47 (Apr. 4, 1986).

L. Lipka et al., "Reduction of LDL–Cholesterol and Elevation of HDL–Cholesterol in Subjects with Primary Hypercholesterolemia by SCH 58235: Pooled Analysis of Two Phase II Studies", *JACC* 257A (Feb. 2000).

Medical Economics, Co., Inc., *Physician's Desk Reference,* 207–208, 2054 (55th Ed. 2001).

K. Fassbender et al., "Simvastatin Strongly Reduces Levels of Alzheimer's Disease β–Amyloid Peptides Aβ 42 and Aβ40 in vitro and in vivo", *PNAs Early Edition,* www.phas.org/cqi/doi/10,1073/phas.081620098 (2001).

Andrx Announces Results of Alzheimer's Disease Clinical Study, *Andrx Corporate Release* (Apr. 11, 2001).

Andrx (ADRX): Pos Phase II Results Using Avicor in Alzheimer's: Str Buy; $130,*US Bancorp Piper,* Apr. 12, 2001.

Statins May Protect Against Alzheimer's Disease; much research needed, *Geriatrics* Feb. 2001.

Dementia and Statins, *The Lancet* Mar. 17, 2001.

Research & Development: Andrx Says Cholesterol Drug May Treat Alzheimers, *Reuters* Apr. 11, 2001.

Cholesterol Drugs Ease Alzheimer's Damage; www.usatoday.com Apr. 10, 2001.

L. Refolo et al, Hypercholesterolemia Accelerates the Alzheimer's Amyloid Pathology in a Transgenic Morse Model, *Neurobiology of Disease* 321–331 (2000).

D. Kang et al., "Modulation of Amyloid β–protein Clearance and Alheimer's Disease Susceptibility by the LDL Receptor—Related Protein Pathway", *Journal of Clinical Investigation* 106:9, 1159–1166 (Nov. 2000).

Y.A. Kesaniewmi, "Intestinal Cholesterol Absorption Efficienty in Man is Related to Apoprotein E Phenotype", *J. Clin. Invest.* 80(2) 578–81 (Aug. 1987).

J. Busciglio et al., "Generation of β–amyloid in the secretary pathway in neuronal and nonneuronal cells", *90 Proc. Nat'l. Acad. Sci, USA,* 2092–2096 *Neurobiology (Mar. 1993).*

L. Farrer et al., "Assessment of Genetic Risk for Alzheimer's Disease Among first Degree Relatives", *Annals of Neurology* 25:5, 485–493 (May 1989).

A. Goate et al., "Segregation of a Missense Mutation in the Amyloid Precursor Protein Gene with Familial Alzheimer's Disease", *349 Nature No. 6311,* 704–706 (Feb. 21, 1991).

D. Mann et al., "The Pattern of Acquisition of Plaques and Tangle in the Brains of Patients Under 50 years of Age with Down's Syndrome", *89 J. Neuro. Sci.,* 169–170 (Feb. 1989).

G. McKhann et al., "Clinical Diagnosis of Alzheimer's Disease", *34 Neurology No. 7,* 939–944 (Jul. 1984).

D. Selokoe, "Alzheimer's Disease: Genotypes, Pheontype and Treatments", *275 Science,* 630–631 (Jan. 31, 1997).

C. Van Duijn, et al., "Familial Aggregation of Alzheimer's Disease and Related Disorders: A collaborative Re–Analysis of Case–Control Studies", *20 Int'l J. Epidemiology No. 2 (Suppl. 2),* 513–520 (1991).

T Nagahara et al., "Dibasic (Amidcinoaryl) Propanoic Acid Derivatives as Novel Blood Coagulation Factor Xa Inhibitors", J. Med. Chem 37:1200–1207 (1994).

Mellott et al., "Acceleration of Recombinant Tissue–Type Plasminogen Activator Induced Reperfusion and Prevention of Reocculsion by Recombinant Antistasin, a selective factor Xa Inhibitor, in a Canine Model of Femoral Arterial Thrombosis", *Circulation Research*, 70:1152–1160 (1992).

Sitko et al., "Conjunctive Enhancement of Enzymatic Thrombolysis and Prevention of Thrombotic Reocclusion With the Selective Factor Xa Inhibitor, Tick Anticoagulant Peptide", *Circulation*, 85:805–815 (1992).

Seymour et al., 1994, *Biochemistry*, 33:3949–3959.

Markwardt, 1994, *Thrombosis and Hemostasis*, 72:477–479.

Mendall et al., "C–Reactive Protein and its relation to cardiovascular risk factor: A population based cross sectional study", *BMJ;* 312:1061–1065 (Apr. 27, 1996).

Ridker P. et al., "Prospective Studies of C–Reactive Protein as a risk factor for cardiovascular disease", 46 *J. Investig. Med.;* 8:391–395 (1998).

L. Gruberb, 2000, "Inflammatory Markers in Acute Coronary Syndromes: C–reative protein (CRP) and Chlamydia", *American Heart Association Scientific Sessions.*

Waters, D. et al., "A Controlled Clinical Trial to Assess the Effect of a Calcium Channel Blocker on the Progression of Coronary Atherosclerosis", *Circulation;* 82:1940–1953 (1990).

Fleckenstein, 1985, *Cir. Res.* vol. 52 (Suppl. 1) 3–16.

Fleckenstein, 1983, "Experimental Facts and Therapeutics Prospects", *John Wiley, New York, pp. 286–313.*

McCall, D., 1985, *Curr. Pract. Cardiol.* vol. 10, 1–11.

Remington 1995, The Science and Practive of Pharmacy, (19$^{th}$ Ed. 1995) p. 963.

M. Chistie et al., "Early—Onset Amyloid Deposition and Cognitive Deficits in Transgenic Mice Expressing a Double Mutant Form of Amyloid Precursor Protein 695", 276 *J. Biol. Chem. No. 24;* 21562–70 (Jun. 15, 2001).

C. Janus et al., "Aβ Peptide Immunization Reduces Behavioral impairment and Plaques in a Model of Alzheimer's Disease", *408 Nature 21/28;* 979–982 (Dec. 2000).

Manual of Laboratory Operations, Lipids Research Clinics Program Report, Washington, D.C., *U.S. Dept. of Health, Education and Welfare Publication;* 1:75–628 (1974).

Steiner, PM et al., Standardization of Micromethods for Plasma Cholesterol, Triglyceride and HDL–Cholesterol with the Lipid Clinic's Methodology [abstract], *J. Clin. Chem. Clin. Bichem;* 19:850 (1981).

Steele WG, et al., Enzymatic Determinations of Cholesterol in High Density Lipoprotein Fractions Prepared by Precipitation Technique,22 *Clin. Chem.;* 1:98–101 (1976).

Salen et al., "Increased Sitosterol Absorption, Decreased Removal and Expanded Body Pools Compensate for Reduced Choelsterol Syntheses in Sitosterolemia with Xanthomatosis", *J. Lipd Res.,;* 30:1319–1330 (1989).

Lutjohann et al., "Sterol Absorption and Sterol Balance in Phytosterolemia Evaluated by Deuterium–Labeled Sterols: Effect of Sitostanol Treatment", *J. Lipid Res.;* 36:8; 1763–1773 (1995).

Zhang et al., "Calpain Inhibitor I Increases B–Amyloid Peptide by Inhibiting the Degradation of the Substrate of γ–Secretase" 274 *J. Biol, Chem.,* 13:8966–8972 (1999).

Zhang et al., "Biochemical Characterization of the γ–Secretase Activity that Produces B–Amyloid Peptides", Biochemistry 40:5049–5055 (2001).

Ida et al., "Analysis of Heterogeneous BA4 Peptides in Human Cerebrospinal Fluid and Blood by a Newly Developed Sensitive Western Blot Assay", 271 *J. Biol, Chem.;* 37:22908–22914 (1996).

Lichtlen, P.R. et al., 1990, *Lancet;* 335:1109–1113.

Bays et al., "Effectiveness and Tolerability of Ezetimibe in Patients with Primary Hypercholesterolemia: Pooled Analysis of Two Phase II Studies", *Clinical Therapeutics,* 23:1209–1230 (2001).

E. Leitersdorf et al., "Cholesterol absorption inhibition: filling an unmet needs in lipid–lowering management", *European Heart Journal Supplement,* 3:E17–E23 (Jun. 2001).

Bauer et al., "Ezetimibe Does not Affect the Pharmacokinetics of Pharmacodynamics of Warfarin", *Clinical Pharmacology and Therapeutics,* 69:2 p5 (Mar. 6–10, 2001).

Keung et al., Ezetimibe Does Not Affect the Pharmacokinetics of oral Contraceptives, *Clinical Pharmacology and Therapeutics,* 69:2 p55 (Mar. 6–10, 2001).

Kosoglou et al., "Pharmacodynamic interaction between fenofibrate and the Cholesterol Absorption Inhibitor Ezetimibe", *Workshops Lipid Lowering Drugs 72$^{nd}$ EAS Congress,* p. 38 (May 21–23, 2001).

T. Kosoglou et al., "Coadministration of Ezetimibe and Fenofibrale Leads to Favorable Effects On Apo CII and LDL Subfractions", *Posters 11. Lipid Lowering Drugs/Novel, 72$^{nd}$ EAS Congress,* p. 89 (May 21–23, 2001).

L. Reyderman et al., "Assessment of a Multiple–Dose Drug Interaction Between Ezetimibe and Gemfibrozil", Presented at XIV Int'l Symp. on Drugs Affecting Lipid Metabolism (DALM) N.Y. (Sep. 9–12, 2001).

P. Statkevich et al., "Ezetimibe Does Not Affect the Pharmacokinetics and Pharmacodynamics of Glipizide", *Clinical Pharmacology & Therapeutics,* 69:67 (Mar. 6–10, 2001).

Knopp et al, "Effect of Ezetimibe on Serum Concentrations of Lipid–Soluble Vitamins", *Posters 11. Lipid Lowering Drug/Novel 72$^{nd}$ EAS Congress,* p. 90 (May 21–23, 2001).

Kosoglou et al., "Pharmacodynamic Interaction Between Fenofibrate and the Cholesterol Absorption Inhibitor Ezetimibe", *Workshops Lipid Lowering Drugs, 72$^{nd}$ EAS Congress,* p. 38 (Mar. 6–10, 2001).

Bays et al., "Low–Density Lipoprotein Cholesterol Reduction By SCH 58235 (Ezetimibe), A Novel Inhibitor of Intestinal Cholesterol Absorption, in 243 Hypercholesterolemic Subjects: Results of a Dose–Response Study", *XII International Symposium on Atherosclerosis, Stockholm, Sweden (Jun. 25–29, 2000).*

Castaner et al, "Ezetimibe—Hypolipidemic Cholesterol Absorption Inhibitor", *Drugs of the Future,* 25(7):679–685 (2000).

Lipka et al., "Reduction of LDL–Cholesterol and Elevation of HDL–Cholesterol in Subjects with Primary Hypercholesterolemia by Ezetimibe (SCH 58235): Pooled Analysis of Two Phase II Studies", *American College of Cardiology Annual Meeting, Anaheim, CA (Mar. 12–15, 2000).*

Van Heek et al., "Comparison of the activity and disposition of the novel cholesterol absorption inhibitor, SCH58235, and its glucuronide, SCH60663", *British Journal of Pharmacology,* 129:1748–1754 (2000).

Van Heek et al., 2000, "The potent cholesterol absorption inhibitor, ezetimibe, is glucuronidated in the intestine, localizes to the intestine, and circulates enteroheatically", *XII International Symposium of Atherosclerosis, Stockholm Sweden* (Jun. 25–29, 2000).

Iannucci et al., "Metabolism of SCH 58235 in the Human, Rat and Dog", *47th ASMS Conference on Mass Spectrometry and Allied Topics, Dallas, TX* (Jun. 13–17, 1999).

Reiss et al., "An Enzymatic Synthesis of Glucuronides of Azetidinone–based Cholesterol Absorption Inhibitors", *Bioorganic & Medicinal Chemistry*, 7:2199–2202 (1999).

Rosenblum et al., "Discovery of 1-(4-Flurophenyl)-(3R)-[3-(-4-fluorophenyl)-(3S)-hydroxypropyl]-(4S)-(4-hydroxyphenyl)-2-azetidinone (SCH 58325): A Designed, Potent, Orally Active Inhibitor of Cholesterol Absorption", *J. Med. Chem.* 41:973–980 (1998).

Vaccaro et al., "Sugar–Substituted 2-Azetidinone Cholesterol Absorption Inhibitors: Enhanced Potency by Modification of the Sugar", *Bioorganic & Medicinal Chemistry Letters*, 8:313–318 (1998).

Zaks et al., "Enzymatic Glucuronidation of a Novel Cholesterol Absorption Inhibitor, SCH 58235", *Applied Biochemistry and Biotechnology*, 73:205–214 (1998).

W. Insull et al., Postmenopausal Hypercholesterolemic Women Derive Additive Benefit from Raloxifene and Simvastatin on Lipid Paramters, *World Heart Federation 6th International Symposium on Global Risk of Coronary Heart Disease and Stroke—Abstract Book*, p. 35 (Jun. 12–15, 2002).

L. Simons et al., 2002, "Ezetimibe added to on–going statin therapy for treatment of primary hypercholesterolemia: Efficacy and safety in patients with Type 2 diabetes mellitus", presented at the 38th Annual Meeting of the EASD, Sep. 1–5, 2002.

C. Allain et al, 1974, "Enzymatic Determination of Total Serum Cholesterol", *Clinical Chemical*, 20:470–475.

R. Mayrhofer et al., 1980, "Simple–Preparation of 3–Benzylidene–2–azetilidinones", *Synthesis*, 247–248.

Burrier, R.E. et al., 1994, "Demonstration of a Direct Effect on Hepatic Acyl CoA:Cholesterol Acyl Transferase (ACAT) Activity By An Orally Administered Enzyme Inhibitor in the Hamster", *Biochemical Pharmacology* 47:1545–1551.

Burrier, R.E. et al., 1994, "The Effect of Acyl CoACholesterol Acyltransferase Inhibitor on the Uptake, Esterification and Secretion of Cholesterol by the Hamster Small Intestine", *The Journal of Pharmacology and Experimental Therapeutics* 272:156–163.

E. F. Binder et al., "Effects of Hormone Replacement Therapy on Serum Lipids in Elderly Women. A Randomized, Placebo–Controlled Trial", *134 Ann. Intern. Med.* 9:754–760 (May. 1, 2001).

MR Haymart et al., "Optimal Management of Dyslipidemia in Women and Men", 2 *J. Gend. Specif. Med.* 6:37–42 (Nov.–Dec. 1997).

"Framingham Heart Study Analysis Reveals Some Primary Prevention Subgroups Are Being Overlooked", *Heartwire* (Apr. 12, 2001).

"Detection Evaluation, and Treatment of High Blood Cholesterol in Adults (Adult Treatment Panel III), Third Report of the National Cholesterol Education Program (NCEP)", *NIH Publication No. 01–3670* (May 2001).

Van Heek et al., "Ezetimibie, A Potent Cholesterol Absorption Inhibitor, Normalizes Combined Dyslipidemia in Obese Hyperinsulinemic Hamsters", 50 *Diabetes* 1330–1335 (Jun. 2001).

"Additional Statins Show Anti–Inflammatory Effect", 103 *Circulation* 1933–35 (Apr. 17, 2001).

H. Hauser, et al, "Identification of a Receptor Mediating Absorption of Dietary Cholesterol in the Intestine", *Biochemistry* 37:17843–17850, 1998.

G. Salen, et al., "Sitosterolemia", *Journal of Lipid Research* 33:945–955, 1992.

P.F. Belamarich et al., "Response to Diet and Cholestyramine in a Patient with Sitosterolemia", *Pediatrics*, 977–981, (Dec. 1990).

G. Salen et al., "Lethal Atherosclerosis Associated With Abnormal Plasma and Tissue Sterol Composition in Sitosterolemia With Xanthomatosis", *Journal of Lipid Research*, 1126–1133, (Sep. 1985).

G.R. Thompson et al., Novel Lipid–Regulating Drugs, Exp. Opin. Invest. Drugs, 9(11):2619–2628, 2000.

* cited by examiner

SUBSTITUTED 2-AZETIDINONES USEFUL AS HYPOCHOLESTEROLEMIC AGENTS

CROSS-REFERENCE TO RELATED APPLICATIONS

This application is a continuation-in-part of U.S. patent application Ser. No. 10/023,295 filed Dec. 17, 2001 now abandoned, which claims the benefit of U.S. Provisional Application Ser. No. 60/256,875 filed Dec. 20, 2000, each incorporated herein by reference.

BACKGROUND OF THE INVENTION

Field of the Invention

The present invention relates to substituted 2-azetidinones useful as hypocholesterolemic agents in the treatment and prevention of atherosclerosis, and to combinations of substituted 2-azetidinone(s) of this invention and cholesterol biosynthesis inhibitor(s) for the treatment and prevention of atherosclerosis.

Atherosclerotic coronary heart disease represents the major cause for death and cardiovascular morbidity in the western world. Risk factors for atherosclerotic coronary heart disease include hypertension, diabetes mellitus, family history, male gender, cigarette smoke and serum cholesterol. A total cholesterol level in excess of 225–250 mg/dl is associated with significant elevation of risk.

"[A] causative link between elevated plasma cholesterol levels, atherosclerosis, and coronary heart disease has been firmly established". Harwood et al., "Pharmacologic Consequences of Cholesterol Absorption Inhibition: Alteration in Cholesterol Metabolism and Reduction in plasma Cholesterol Concentration Induced by the Synthetic Saponin β-tigogenin cellobioside (CP-88818; tiqueside)", 34 *J. Lipid Research* 377–378 (1993).

"The abnormal metabolism and elevation of plasma cholesterol and lipoproteins are well-documented risk factors for the development of atherosclerosis. Evidence from clinical trials indicates that reducing plasma cholesterol by dietary and/or pharmacological means leads to reductions in the incidence of death from cardiovascular disease." Davis, H. R., et al., "Ezetimibe, a potent cholesterol absorption inhibitor, inhibits the development of atherosclerosis in Apo E knockout mice", 21 Arterioeoler. Thromb. Vasc. Biol. 2032–2038 (2001).

Cholesteryl esters are a major component of atherosclerotic lesions and the major storage form of cholesterol in arterial wall cells. Formation of cholesteryl esters is also a key step in the intestinal absorption of dietary cholesterol. In addition to regulation of dietary cholesterol, the regulation of whole-body cholesterol homeostasis in humans and animals involves modulation of cholesterol biosynthesis, bile acid biosynthesis, and the catabolism of the cholesterol-containing plasma lipoproteins. The liver is the major organ responsible for cholesterol biosynthesis and catabolism and, for this reason, it is a prime determinant of plasma cholesterol levels. The liver is the site of synthesis and secretion of very low density lipoproteins (VLDL) which are subsequently metabolized to low density lipoproteins (LDL) in the circulation. LDL are the predominant cholesterol-carrying lipoproteins in the plasma and an increase in their concentration is correlated with increased atherosclerosis.

When cholesterol absorption in the intestines is reduced, by whatever means, less cholesterol is delivered to the liver. The consequence of this action is a decreased hepatic lipoprotein (VLDL) production and an increase in the hepatic clearance of plasma cholesterol, mostly as LDL. Thus, the net effect of an inhibition of intestinal cholesterol absorption is a decrease in plasma cholesterol levels.

Several 2-azetidinone compounds have been reported as being useful in lowering cholesterol and/or in inhibiting the formation of cholesterol-containing lesions in mammalian arterial walls: WO 93/02048 describes 2-azetidinone compounds wherein the 3-position substituent is arylalkylene, arylalkenylene or arylalkylene wherein the alkylene, alkenylene or alkylene portion is interrupted by a hetero atom, phenylene or cycloalkylene; WO 94/17038 describes 2-azetidinone compounds wherein the 3-position substituent is an arylalkylspirocyclic group; WO 95/08532 describes 2-azetidinone compounds wherein the 3-position substituent is an arylalkylene group substituted in the alkylene portion by a hydroxy group; PCT/US95/03196 describes compounds wherein the 3-position substituent is an aryl(oxo or thio)alkylene group substituted in the alkylene portion by a hydroxy group; U.S. Pat. No. 5,633,246 describes the preparation of compounds wherein the 3-position substituent is an arylalkylene group substituted in the alkylene portion by a hydroxy group, and wherein the alkylene group is attached to the azetidinone ring by a —$S(O)_{0-2}$— group; and U.S. Pat. No. 5,756,470 discloses 2-azetidinones having an aryl group at the 4 position which is substituted with a glucuronide group, each of which is incorporated herein by reference.

Also, European Patent 199,630B1 and European Patent Application 337,549A1 disclose elastase inhibitory substituted azetidinones useful in treating inflammatory conditions resulting in tissue destruction which are associated with various disease states, e.g., atherosclerosis.

Other known hypocholesterolemics include plant extracts such as sapogenins, in particular tigogenin and diosgenin. Glycoside derivatives of tigogenin and/or diosgenin are disclosed in WO 94/00480 and WO 95/18143.

The inhibition of cholesterol biosynthesis by 3-hydroxy-3-methyl-glutaryl coenzyme A reductase (EC1.1.1.34) inhibitors has been shown to be an effective way to reduce plasma cholesterol (Witzum, *Circulation*, 80, 5 (1989), p. 1101–1114) and reduce atherosclerosis. Combination therapy of an HMG CoA reductase inhibitor and a bile acid sequestrant has been demonstrated to be more effective in human hyperlipidemic patients than either agent in monotherapy (Illingworth, *Drugs*, 36 (Suppl. 3) (1988), p. 63–71).

SUMMARY OF THE INVENTION

The present invention relates to substituted 2-azetidinones, especially to glucose-derived conjugates of cholesterol-lowering 2-azetidinones having an aryl or substituted aryl group as a substituent at the 1-position and having a hydroxy-substituted phenyl group, especially a 4-hydroxyphenyl group, at the 4-position. Examples of sugars useful as substituents in the present invention include but are not limited to hexose derivatives and ribose derivatives.

In one embodiment, the present invention is directed to a compound represented by the Formula (IA):

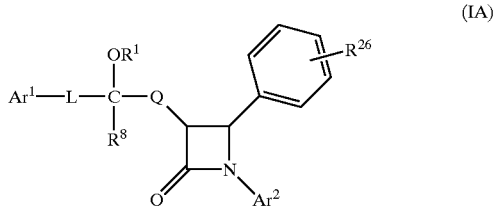

(IA)

or a pharmaceutically acceptable salt or solvate thereof, wherein in Formula (IA):

$R^1$ is selected from the group consisting of H, G, $G^1$, $G^2$, —$SO_3H$ and —$PO_3H$;

G is selected from the group consisting of: H,

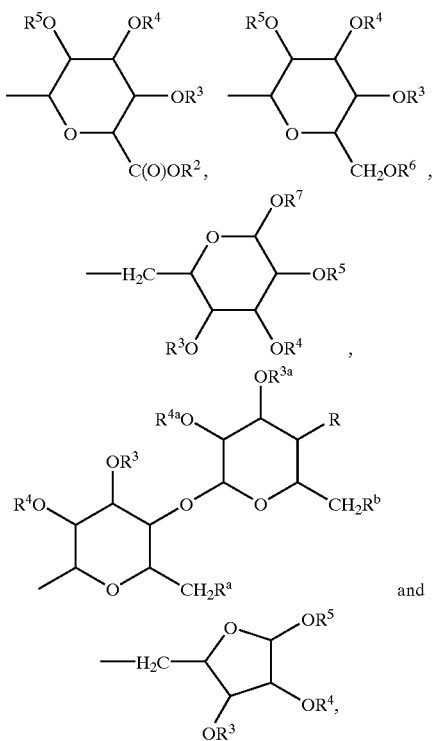

(sugar derivatives)

wherein R, $R^a$ and $R^b$ are each independently selected from the group consisting of H, —OH, halo, —$NH_2$, azido, ($C_1$-$C_6$)alkoxy($C_1$-$C_6$)alkoxy or —W—$R^{30}$;

W is independently selected from the group consisting of —NH—C(O)—, —O—C(O)—, —O—C(O)—N($R^{31}$)—, —NH—C(O)—N($R^{31}$)— and —O—C(S)—N($R^{31}$)—;

$R^2$ and $R^6$ are each independently selected from the group consisting of H, ($C_1$-$C_6$)alkyl, acetyl, aryl and aryl($C_1$-$C_6$)alkyl;

$R^3$, $R^4$, $R^5$, $R^7$, $R^{3a}$ and $R^{4a}$ are each independently selected from the group consisting of H, ($C_1$-$C_6$)alkyl, acetyl, aryl($C_1$-$C_6$)alkyl, —C(O)($C_1$-$C_6$)alkyl and —C(O)aryl;

$R^{30}$ is independently selected from the group consisting of $R^{32}$-substituted T, $R^{32}$-substituted-T-($C_1$-$C_6$)alkyl, $R^{32}$-substituted-($C_2$-$C_4$)alkenyl, $R^{32}$-substituted-($C_1$-$C_6$)alkyl, $R^{32}$-substituted-($C_3$-C7)cycloalkyl and $R^{32}$-substituted-($C_3$-C7)cycloalkyl($C_1$-$C_6$)alkyl;

$R^{31}$ is independently selected from the group consisting of H and ($C_1$-$C_4$)alkyl;

T is independently selected from the group consisting of phenyl, furyl, thienyl, pyrrolyl, oxazolyl, isoxazolyl, thiazolyl, isothiazolyl, benzothiazolyl, thiadiazolyl, pyrazolyl, imidazolyl and pyridyl;

$R^{32}$ is independently selected from 1–3 substituents which are each independently selected from the group consisting of H, halo, ($C_1$-$C_4$)alkyl, —OH, phenoxy, —$CF_3$, —$NO_2$, ($C_1$-$C_4$)alkoxy, methylenedioxy, oxo, ($C_1$-$C_4$)alkylsulfanyl, ($C_1$-$C_4$)alkylsulfinyl, ($C_1$-$C_4$)alkylsulfonyl, —N($CH_3$)$_2$, —C(O)—NH($C_1$-$C_4$)alkyl, —C(O)—N(($C_1$-$C_4$)alkyl)$_2$, —C(O)—($C_1$-$C_4$)alkyl, —C(O)—($C_1$-$C_4$)alkoxy and pyrrolidinylcarbonyl; or $R^{32}$ is a covalent bond and $R^{31}$, the nitrogen to which it is attached and $R^{32}$ form a pyrrolidinyl, piperidinyl, N-methyl-piperazinyl, indolinyl or morpholinyl group, or a ($C_1$-$C_4$)alkoxycarbonyl-substituted pyrrolidinyl, piperidinyl, N-methylpiperazinyl, indolinyl or morpholinyl group;

$G^1$ is represented by the structure:

wherein $R^{33}$ is independently selected from the group consisting of unsubstituted alkyl, $R^{34}$-substituted alkyl, ($R^{35}$)($R^{36}$)alkyl-,

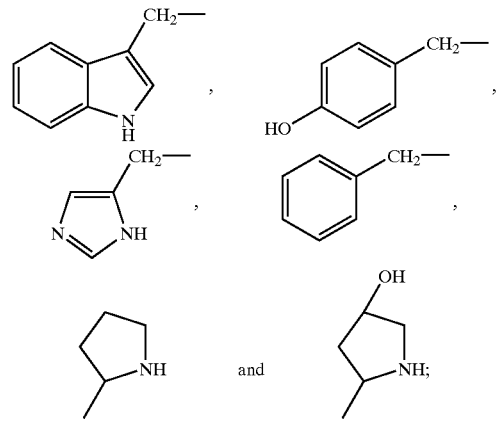

$R^{34}$ is one to three substituents, each $R^{34}$ being independently selected from the group consisting of HOOC—, HS—, ($CH_3$)S—, $H_2N$—, ($NH_2$)(NH)C(NH)—, ($NH_2$)C(O)— and HOOCCH($NH_3^+$)$CH_2$SS—;

$R^{35}$ is independently selected from the group consisting of H and $NH_2$—;

$R^{36}$ is independently selected from the group consisting of H, unsubstituted alkyl, $R^{34}$-substituted alkyl, unsubstituted cycloalkyl and $R^{34}$-substituted cycloalkyl;

$G^2$ is represented by the structure:

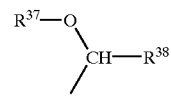

wherein $R^{37}$ and $R^{38}$ are each independently selected from the group consisting of ($C_1$-$C_6$)alkyl and aryl;

$R^{26}$ is one to five substituents, each $R^{26}$ being independently selected from the group consisting of:

a) H;

b) —OH;

c) —OCH$_3$;
d) fluorine;
e) chlorine;
f) —O-G;
g) —O-G$^1$;
h) —O-G$^2$;
i) —SO$_3$H; and
j) —PO$_3$H;
provided that when R$^1$ is H, R$^{26}$ is not H, —OH, —OCH$_3$ or —O-G;

Ar$^1$ is aryl, R$^{10}$-substituted aryl, heteroaryl or R$^{10}$-substituted heteroaryl;

Ar$^2$ is aryl, R$^{11}$-substituted aryl, heteroaryl or R$^{11}$-substituted heteroaryl;

L is selected from the group consisting of:
a) a covalent bond;
b) —(CH$_2$)$_q$—, wherein q is 1–6;
c) —(CH$_2$)$_e$-E-(CH$_2$)$_r$—, wherein E is —O—, —C(O)—, phenylene, —NR$^{22}$— or —S(O)$_{0-2}$—, e is 0–5 and r is 0–5, provided that the sum of e and r is 1–6;
d) —(C$_2$–C$_6$)alkenylene-;
e) —(CH$_2$)$_f$—V—(CH$_2$)$_g$—, wherein V is C$_3$–C$_6$cycloalkylene, f is 1–5 and g is 0–5, provided that the sum of f and g is 1–6; and
f)

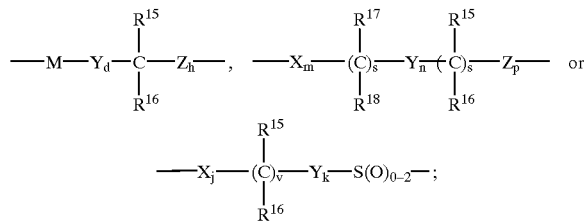

wherein M is —O—, —S—, —S(O)— or —S(O)$_2$—;

X, Y and Z are each independently selected from the group consisting of —CH$_2$—, —CH(C$_1$–C$_6$)alkyl- and —C(di-(C$_1$–C$_6$)alkyl)-;

R$^8$ is selected from the group consisting of H and alkyl;

R$^{10}$ and R$^{11}$ are each independently selected from the group consisting of 1–3 substituents which are each independently selected from the group consisting of (C$_1$–C$_6$)alkyl, —OR$^{19}$, —O(CO)R$^{19}$, —O(CO)OR$^{21}$, —O(CH$_2$)$_{1-5}$OR$^{19}$, —O(CO)NR$^{19}$R$^{20}$, —NR$^{19}$R$^{20}$, —NR$^{19}$(CO)R$^{20}$, —NR$^{19}$(CO)OR$^{21}$, —NR$^{19}$(CO)NR$^{20}$R$^{25}$, —NR$^{19}$SO$_2$R$^{21}$, —COOR$^{19}$, —CONR$^{19}$R$^{20}$, —COR$^{19}$, —SO$_2$NR$^{19}$R$^{20}$, S(O)$_{0-2}$R$^{21}$, —O(CH$_2$)$_{1-10}$—COOR$^{19}$, —O(CH$_2$)$_{1-10}$CONR$^{19}$R$^{20}$, —(C$_1$–C$_6$ alkylene)-COOR$^{19}$, —CH=CH—COOR$^{19}$, —CF$_3$, —CN, —NO$_2$ and halo;

R$^{15}$ and R$^{17}$ are each independently selected from the group consisting of —OR$^{19}$, —OC(O)R$^{19}$, —OC(O)OR$^{21}$, —OC(O)NR$^{19}$R$^{20}$;

R$^{16}$ and R$^{18}$ are each independently selected from the group consisting of H, (C$_1$–C$_6$)alkyl and aryl;

or R$^{15}$ and R$^{16}$ together are =O, or R$^{17}$ and R$^{18}$ together are =O;

d is 1, 2 or 3;
h is 0, 1, 2, 3 or 4;
s is 0 or 1;
t is 0 or 1;
m, n and p are each independently selected from 0–4; provided that at least one of s and t is 1, and the sum of m, n, p, s and t is 1–6; provided that when p is 0 and t is 1, the sum of m, n and p is 1–5; and provided that when p is 0 and s is 1, the sum of m, t and n is 1–5;

v is 0 or 1;

j and k are each independently 1–5, provided that the sum of j, k and v is 1–5;

Q is a bond, —(CH$_2$)$_q$—, wherein q is 1–6, or, with the 3-position ring carbon of the azetidinone, forms the spiro group

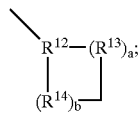

wherein R$^{12}$ is

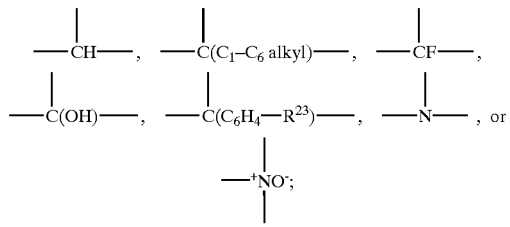

R$^{13}$ and R$^{14}$ are each independently selected from the group consisting of —CH$_2$—, —CH(C$_1$–C$_6$ alkyl)-, —C(di-(C$_1$–C$_6$)alkyl), —CH=CH— and —C(C$_1$–C$_6$ alkyl)=CH—; or R$^{12}$ together with an adjacent R$^{13}$, or R$^{12}$ together with an adjacent R$^{14}$, form a —CH=CH— or a —CH=C(C$_1$–C$_6$ alkyl)- group;

a and b are each independently 0, 1, 2 or 3, provided both are not zero; provided that when R$^{13}$ is —CH=CH— or —C(C$_1$–C$_6$ alkyl)=CH—, a is 1; provided that when R$^{14}$ is —CH=CH— or —C(C$_1$–C$_6$ alkyl)=CH—, b is 1; provided that when a is 2 or 3, the R$^{13}$'s can be the same or different; and provided that when b is 2 or 3, the R$^{14}$'s can be the same or different;

and when Q is a bond and L is

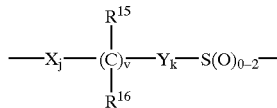

then Ar$^1$ can also be pyridyl, isoxazolyl, furanyl, pyrrolyl, thienyl, imidazolyl, pyrazolyl, thiazolyl, pyrazinyl, pyrimidinyl or pyridazinyl;

R$^{19}$ and R$^{20}$ are each independently selected from the group consisting of H, (C$_1$–C$_6$)alkyl, aryl and aryl-substituted (C$_1$–C$_6$)alkyl;

R$^{21}$ is (C$_1$–C$_6$)alkyl, aryl or R$^{24}$-substituted aryl;

R$^{22}$ is H, (C$_1$–C$_6$)alkyl, aryl (C$_1$–C$_6$)alkyl, —C(O)R$^{19}$ or —COOR$^{19}$;

R$^{23}$ and R$^{24}$ are each independently selected from the group consisting of 1–3 substituents which are independently selected from the group consisting of H, (C$_1$–C$_6$)alkyl, (C$_1$–C$_6$)alkoxy, —COOH, NO$_2$, —NR$^{19}$R$^{20}$, —OH and halo; and R$^{25}$ is H, —OH or (C$_1$–C$_6$)alkoxy.

In another embodiment, compounds of the present invention are represented by the formula I:

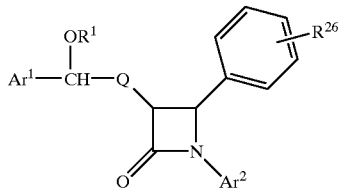

or a pharmaceutically acceptable salt or solvate thereof, wherein $R^{26}$ is selected from the group consisting of:

a) H;
b) —OH;
c) —OCH$_3$;
d) fluorine;
e) chlorine;
f) —O-G;
g) —O-G$^1$; and
h) —SO$_3$H;

provided that when $R^1$ is H, $R^{26}$ is not H, —OH, —OCH$_3$ or —O-G;

$R^1$ is selected from the group consisting of

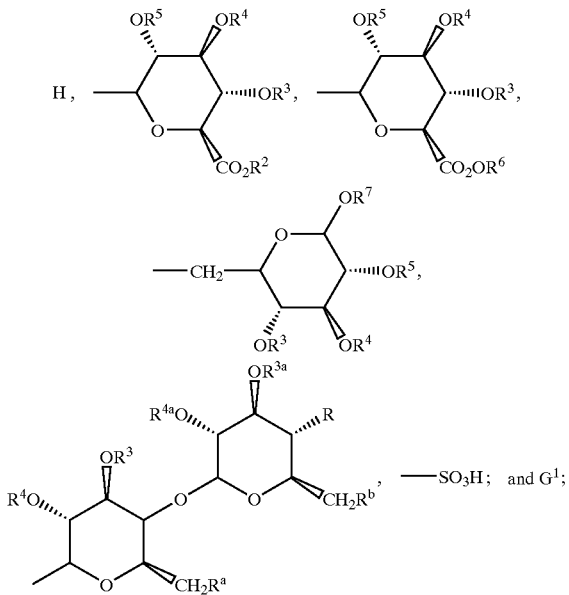

wherein G$^1$ is represented by the structure:

wherein $R^{33}$ is independently selected from the group consisting of unsubstituted alkyl, $R^{34}$-substituted alkyl, ($R^{35}$)($R^{36}$)alkyl-,

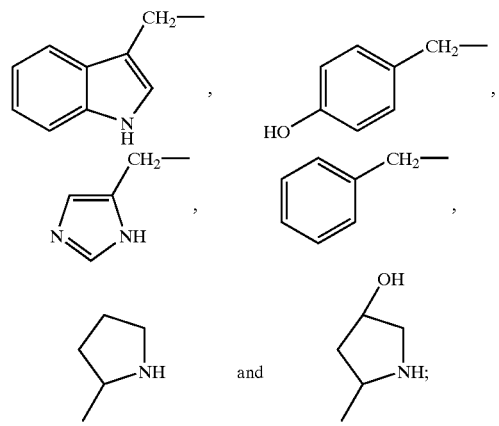

$R^{34}$ is one to three substituents, each $R^{34}$ being independently selected from the group consisting of HOOC—, HS—, (CH$_3$)S—, H$_2$N—, (NH$_3$)(NH)C(NH)—, (NH$_2$)C(O)— and HOOCCH(NH$_3^+$)CH$_2$SS—;

$R^{35}$ is independently selected from the group consisting of H and NH$_2$—;

$R^{36}$ is independently selected from the group consisting of H, unsubstituted alkyl, $R^{34}$-substituted alkyl, unsubstituted cycloalkyl and $R^{34}$-substituted cycloalkyl;

R, $R^a$ and $R^b$ are each independently selected from the group consisting of H, —OH, halogeno, —NH$_2$, azido, (C$_1$–C$_6$)alkoxy(C$_1$–C$_6$)-alkoxy and —W—R$^{30}$;

W is independently selected from the group consisting of —NH—C(O)—, —O—C(O)—, —O—C(O)—N(R$^{31}$)—, —NH—C(O)—N(R$^{31}$)— and —O—C(S)—N(R$^{31}$)—;

$R^2$ and $R^6$ are each independently selected from the group consisting of H, (C$_1$–C$_6$)alkyl, aryl and aryl(C$_1$–C$_6$)alkyl;

$R^3$, $R^4$, $R^5$, $R^7$, $R^{3a}$ and $R^{4a}$ are each independently selected from the group consisting of H, (C$_1$–C$_6$)alkyl, aryl(C$_1$–C$_6$)alkyl, —C(O)(C$_1$–C$_6$)alkyl and —C(O)aryl;

$R^{30}$ is independently selected form the group consisting of $R^{32}$-substituted T, $R^{32}$-substituted-T-(C$_1$–C$_6$)alkyl, $R^{32}$-substituted-(C$_2$–C$_4$)alkenyl, $R^{32}$-substituted-(C$_1$–C$_6$)alkyl, $R^{32}$-substituted-(C$_3$–C7)cycloalkyl and $R^{32}$-substituted-(C$_3$–C7)cycloalkyl(C$_1$–C$_6$)alkyl;

$R^{31}$ is independently selected from the group consisting of H and (C$_1$–C$_4$)alkyl;

T is independently selected from the group consisting of phenyl, furyl, thienyl, pyrrolyl, oxazolyl, isoxazolyl, thiazolyl, isothiazolyl, benzothiazolyl, thiadiazolyl, pyrazolyl, imidazolyl and pyridyl;

$R^{32}$ is independently selected from 1–3 substituents independently selected from the group consisting of H, halogeno, (C$_1$–C$_4$)alkyl, —OH, phenoxy, —CF$_3$, —NO$_2$, (C$_1$–C$_4$)alkoxy, methylenedioxy, oxo, (C$_1$–C$_4$)alkylsulfanyl, (C$_1$–C$_4$)alkylsulfinyl, (C$_1$–C$_4$)alkylsulfonyl, —N(CH$_3$)$_2$, —C(O)—NH(C$_1$–C$_4$)alkyl, —C(O)—N((C$_1$–C$_4$)alkyl)$_2$, —C(O)—(C$_1$–C$_4$)alkyl, —C(O)—(C$_1$–C$_4$)alkoxy and pyrrolidinylcarbonyl; or $R^{32}$ is a covalent bond and $R^{31}$, the nitrogen to which it is attached and $R^{32}$ form a pyrrolidinyl, piperidinyl, N-methyl-piperazinyl, indolinyl or morpholinyl group, or a (C$_1$–C$_4$)alkoxycarbonyl-substituted pyrrolidinyl, piperidinyl, N-methylpiperazinyl, indolinyl or morpholinyl group;

Ar$^1$ is aryl, $R^{10}$-substituted aryl, heteroaryl or $R^{10}$-substituted heteroaryl;

Ar$^2$ is aryl, $R^{11}$-substituted aryl, heteroaryl or $R^{11}$-substituted heteroaryl;

Q is —(CH$_2$)$_q$—, wherein q is 2–6, or, with the 3-position ring carbon of the azetidinone, forms the spiro group

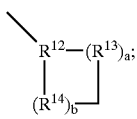

$R^{12}$ is

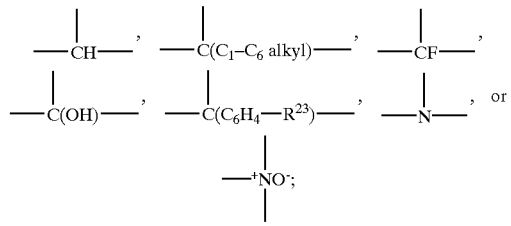

$R^{13}$ and $R^{14}$ are independently selected from the group consisting of —$CH_2$—, —$CH(C_1-C_6$ alkyl)-, —$C(di-(C_1-C_6)$alkyl), —CH=CH— and —$C(C_1-C_6$ alkyl)=CH—; or $R^{12}$ together with an adjacent $R^{13}$, or $R^{12}$ together with an adjacent $R^{14}$, form a —CH=CH— or a —CH=$C(C_1-C_6$ alkyl)- group;

a and b are independently 0, 1, 2 or 3, provided both are not zero; provided that when $R^{13}$ is —CH=CH— or —$C(C_1-C_6$ alkyl)=CH—, a is 1; provided that when $R^{14}$ is —CH=CH— or —$C(C_1-C_6$ alkyl)=CH—, b is 1; provided that when a is 2 or 3, the $R^{13}$'s can be the same or different; and provided that when b is 2 or 3, the $R^{14}$'s can be the same or different;

$R^{10}$ and $R^{11}$ are independently selected from the group consisting of 1–3 substituents independently selected from the group consisting of $(C_1-C_6)$alkyl, —$OR^{19}$, —$O(CO)R^{19}$, —$O(CO)OR^{21}$, —$O(CH_2)_{1-5}OR^{19}$, —$O(CO)NR^{19}R^{20}$, —$NR^{19}R^{20}$, —$NR^{19}(CO)R^{20}$, —$NR^{19}(CO)OR^{21}$, —$NR^{19}(CO)NR^{20}R^{25}$, —$NR^{19}SO_2R^{21}$, —$COOR^{19}$, —$CONR^{19}R^{20}$, —$COR^{19}$, —$SO_2NR^{19}R^{20}$, $S(O)_{0-2}R^{21}$, —$O(CH_2)_{1-10}$—$COOR^{19}$, —$O(CH_2)_{1-10}CONR^{19}R^{20}$, —$(C_1-C_6$ alkylene)—$COOR^{19}$, —CH=CH—$COOR^{19}$, —$CF_3$, —CN, —$NO_2$ and halogen;

$R^{19}$ and $R^{20}$ are independently selected from the group consisting of H, $(C_1-C_6)$alkyl, aryl and aryl-substituted $(C_1-C_6)$alkyl;

$R^{21}$ is $(C_1-C_6)$alkyl, aryl or $R^{24}$-substituted aryl;

$R^{22}$ is H, $(C_1-C_6)$alkyl, aryl $(C_1-C_6)$alkyl, —$C(O)R^{19}$ or —$COOR^{19}$;

$R^{23}$ and $R^{24}$ are independently 1–3 groups independently selected from the group consisting of H, $(C_1-C_6)$alkyl, $(C_1-C_6)$alkoxy, —COOH, $NO_2$, —$NR^{19}R^{20}$, —OH and halogeno; and $R^{25}$ is H, —OH or $(C_1-C_6)$alkoxy.

In another aspect, the present invention is directed to a method of treating or preventing a vascular condition, diabetes, obesity or lowering concentration of a sterol in plasma of a mammal, comprising administering to a mammal in need of such treatment an effective amount of a compound of formula I and/or formula IA.

This invention also relates to methods of using substituted 2-azetidinone(s), especially of formula I and/or IA, for treating or preventing atherosclerosis or reducing plasma cholesterol levels comprising administering to a mammal in need of such treating, preventing or reducing an effective amount of a compound of formula I and/or IA.

In another aspect, the invention relates to a pharmaceutical composition comprising a substituted 2-azetidinone of formula I and/or IA and a pharmaceutically acceptable carrier.

In another embodiment, the present invention also relates to a method of reducing hepatic cholesterol ester levels, a method of reducing plasma cholesterol levels, and to a method of treating or preventing atherosclerosis, comprising administering to a mammal in need of such treatment an effective amount of a combination of a substituted 2-azetidinone of formula I and/or IA and a cholesterol biosynthesis inhibitor. That is, one aspect of the present invention relates to the use of a substituted 2-azetidinone of Formula I and/or IA in combination with a cholesterol biosynthesis inhibitor (and, similarly, use of a cholesterol biosynthesis inhibitor in combination with a substituted 2-azetidinone of Formula I and/or IA) to treat or prevent atherosclerosis or to reduce plasma cholesterol levels.

In yet another aspect, the invention relates to a pharmaceutical composition comprising an effective amount of a combination of a substituted 2-azetidinone of Formula I and/or IA and a cholesterol biosynthesis inhibitor and a pharmaceutically acceptable carrier.

In a another aspect, the invention relates to a kit comprising in one container an effective amount of a substituted 2-azetidinone of Formula I and/or IA in a pharmaceutically acceptable carrier, and in a separate container, an effective amount of a cholesterol biosynthesis inhibitor in a pharmaceutically acceptable carrier.

Other than in the operating examples, or where otherwise indicated, all numbers expressing quantities of ingredients, reaction conditions, and so forth used in the specification and claims are to be understood as being modified in all instances by the term "about."

DETAILED DESCRIPTION

As used above, and throughout the specification, the following terms, unless otherwise indicated, shall be understood to have the following meanings:

"Patient" includes both human and other animals.

"Mammal" includes humans and other mammalian animals.

The following definitions apply regardless of whether a term is used by itself or in combination with other terms, unless otherwise indicated. Therefore, the definition of "alkyl" applies to "alkyl" as well as the "alkyl" portions of "hydroxyalkyl", "haloalkyl", "alkoxy", etc.

As used herein, the term "alkyl" means an aliphatic hydrocarbon group which may be straight or branched and comprising 1 to about 20 carbon atoms in the chain. Preferred alkyl groups comprise 1 to about 12 carbon atoms in the chain. More preferred alkyl groups comprise 1 to about 6 carbon atoms in the chain. "Branched" means that one or more lower alkyl groups such as methyl, ethyl or propyl, are attached to a linear alkyl chain. "Lower alkyl" means a group having about 1 to about 6 carbon atoms in a chain that may be straight or branched. The alkyl can be substituted and the term "substituted alkyl" means that the alkyl group is substituted by one or more substituents independently selected from the group consisting of halo, aryl, cycloalkyl, cyano, hydroxy, alkoxy, alkylthio, amino, —NH(alkyl), —NH(cycloalkyl), —N(alkyl)$_2$ (which alkyls can be the same or different), carboxy and —C(O)O-alkyl. Non-limiting examples of suitable alkyl groups include methyl, ethyl, n-propyl, isopropyl, n-butyl, t-butyl, n-pentyl, heptyl, nonyl, decyl, fluoromethyl, trifluoromethyl and cyclopropylmethyl.

"Alkoxy" means an alkyl-O— group in which the alkyl group is as previously described. Useful alkoxy groups can comprise 1 to about 12 carbon atoms, preferably 1 to about 6 carbon atoms. Non-limiting examples of suitable alkoxy groups include methoxy, ethoxy and isopropoxy. The alkyl group of the alkoxy is linked to an adjacent moiety through the ether oxygen.

"Alkylsulfanyl" or "alkylthio" means an alkyl-S— group in which the alkyl group is as previously described. Non-limiting examples of suitable alkylsulfanyl groups include methylthio, ethylthio and isopropylthio. The alkyl is linked to an adjacent moiety through the sulfur.

"Alkylsulfinyl" means an alkyl-S(O)— group. Preferred groups are those in which the alkyl group is lower alkyl. The alkyl is linked to an adjacent moiety through the sulfinyl.

"Alkylsulfonyl" means an alkyl-S($O_2$)— group. Preferred groups are those in which the alkyl group is lower alkyl. The alkyl is linked to an adjacent moiety through the sulfonyl.

"Alkenyl" means an aliphatic hydrocarbon group (straight or branched carbon chain) comprising one or more double bonds in the chain and which can be conjugated or unconjugated. Useful alkenyl groups can comprise 2 to about 15 carbon atoms in the chain, preferably 2 to about 12 carbon atoms in the chain, and more preferably 2 to about 6 carbon atoms in the chain. "Lower alkenyl" means 2 to about 6 carbon atoms in the chain which can be straight or branched. The alkenyl group can be substituted and the term "substituted alkenyl" means that the alkenyl group is substituted by one or more substituents independently selected from the group consisting of halo, alkyl, aryl, cycloalkyl, cyano and alkoxy. Non-limiting examples of suitable alkenyl groups include ethenyl, propenyl, n-butenyl, 3-methylbut-enyl and n-pentenyl.

Where an alkyl or alkenyl chain joins two other variables and is therefore bivalent, the terms alkylene and alkenylene, respectively, are used.

"Aryl" means an aromatic monocyclic or multicyclic ring system comprising about 5 to about 14 carbon atoms, preferably about 6 to about 10 carbon atoms. The aryl group can be substituted with one or more "ring system substituents" which may be the same or different, and are as defined herein. Non-limiting examples of suitable aryl groups include phenyl, naphthyl, indenyl, tetrahydronaphthyl and indanyl. "Phenylene" means a bivalent phenyl group, including ortho, meta and para-substitution.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, phenethyl and naphthlenylmethyl. The aralkyl is linked to an adjacent moiety through the alkyl group.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be substituted with one or more "ring system substituents" which may be the same or different, and are as defined below. Non-limiting examples of suitable monocyclic cycloalkyls include cyclopropyl, cyclobutyl, cyclopentyl, cyclohexyl and the like. Non-limiting examples of suitable multicyclic cycloalkyls include 1-decalinyl, norbornyl, adamantyl and the like. "Cycloalkylene" refers to a corresponding bivalent ring, wherein the points of attachment to other groups include all positional isomers.

"Halo" or "halogeno" refers to fluorine, chlorine, bromine or iodine radicals. Preferred are fluoro, chloro or bromo, and more preferred are fluoro and chloro.

"Heteroaryl" means a monocyclic or multicyclic aromatic ring system of about 5 to about 14 ring atoms, preferably about 5 to about 10 ring atoms, in which one or more of the atoms in the ring system is/are atoms other than carbon, for example nitrogen, oxygen or sulfur. The heteroatom(s) interrupt a carbocyclic ring structure and have a sufficient number of delocalized pi electrons to provide aromatic character, provided that the rings do not contain adjacent oxygen and/or sulfur atoms. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be oxidized to form the corresponding N-oxide. All regioisomers are contemplated, e.g., 2-pyridyl, 3-pyridyl and 4-pyridyl. Examples of useful 6-membered heteroaryl groups include pyridyl, pyrimidinyl, pyrazinyl, pyridazinyl and the like and the N-oxides thereof. Examples of useful 5-membered heteroaryl rings include furyl, thienyl, pyrrolyl, thiazolyl, isothiazolyl, imidazolyl, pyrazolyl and isoxazolyl. Useful bicyclic groups are benzo-fused ring systems derived from the heteroaryl groups named above, e.g., quinolyl, phthalazinyl, quinazolinyl, benzofuranyl, benzothienyl and indolyl.

"Ring system substituent" means a substituent attached to an aromatic or non-aromatic ring system which, for example, replaces an available hydrogen on the ring system. Ring system substituents may be the same or different, each being independently selected from the group consisting of aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $Y_1Y_2N$—, $Y_1Y_2N$-alkyl-, $Y_1Y_2NC(O)$— and $Y_1Y_2NSO_2$—, wherein $Y_1$ and $Y_2$ may be the same or different and are independently selected from the group consisting of hydrogen, alkyl, aryl, and aralkyl.

$R^{24}$-benzyl and $R^{24}$-benzyloxy refer to benzyl and benzyloxy radicals which are substituted on the phenyl ring.

The above statements, wherein, for example, $R^{19}$ and $R^{20}$ are said to be independently selected from a group of substituents, means that $R^{19}$ and $R^{20}$ are independently selected, but also that where an $R^{19}$ or $R^{20}$ variable occurs more than once in a molecule, those occurrences are independently selected (e.g., if $R^{10}$ is —$OR^{19}$ wherein $R^{19}$ is hydrogen, $R^{11}$ can be —$OR^{19}$ wherein $R^{19}$ is lower alkyl). Those skilled in the art will recognize that the size and nature of the substituent(s) will affect the number of substituents which can be present.

The phrases "effective amount" and "therapeutically effective amount" mean that amount of a compound of Formula I and/or IA, and other pharmacological or therapeutic agents described below, that will elicit a biological or medical response of a tissue, system, animal or mammal that is being sought by the administrator (such as a researcher, doctor or veterinarian) which includes alleviation of the symptoms of the condition or disease being treated and the prevention, slowing or halting of progression of one or more conditions, for example vascular conditions, such as hyperlipidaemia (for example atherosclerosis, hypercholesterolemia or sitosterolemia), vascular inflammation, stroke, diabetes, obesity and/or to reduce the level of sterol(s) (such as cholesterol) in the plasma. As used herein, "vascular" comprises cardiovascular, cerebrovascular and combinations thereof.

The compounds, compositions and treatments of the present invention can be administered by any suitable means which produce contact of these compounds with the site of action in the body, for example in the plasma, liver or small intestine of a mammal or human.

As used herein, "sterol absorption inhibitor" means a compound capable of inhibiting the absorption of one or more sterols, including but not limited to cholesterol, phytosterols (such as sitosterol, campesterol, stigmasterol and avenosterol), 5α-stanols (such as cholestanol, 5α-campestanol, 5α-sitostanol), and mixtures thereof, when administered in a therapeutically effective (sterol absorption inhibiting) amount to a patient or human.

In one embodiment of the present invention, $R^1$ is selected from the group consisting of G, $G^1$ and $G^2$. Preferably $R^1$ is G.

In another embodiment of the present invention, G is selected from the group consisting of:

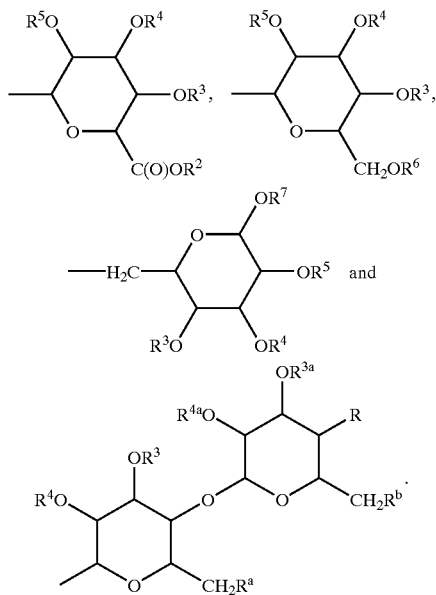

In another embodiment of the present invention, G is selected from the group consisting of

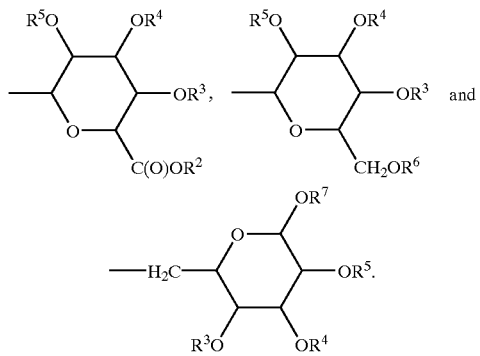

In yet another embodiment of the present invention, G is selected from the group consisting of:

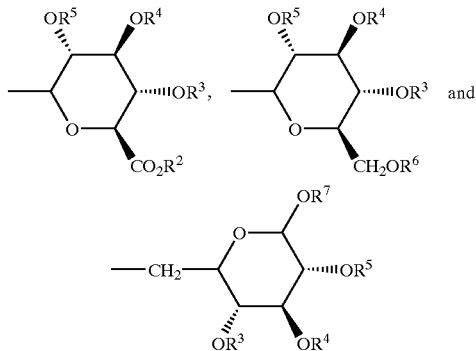

wherein:
$R^2$, $R^3$, $R^4$, $R^5$, $R^6$ and $R^7$ are each independently selected from the group consisting of H, $(C_1-C_6)$alkyl, benzyl and acetyl.

In another embodiment of the present invention, G is:

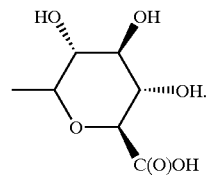

In another embodiment of the present invention, G is:

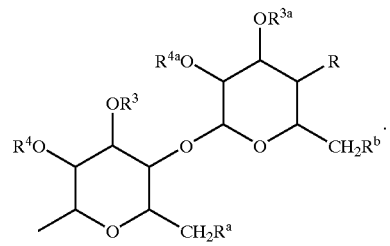

In another embodiment of the present invention, G is:

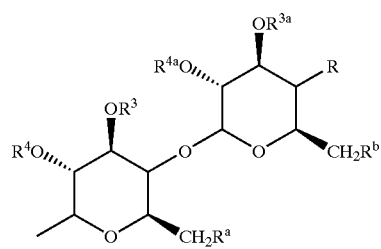

wherein:
$R^3$, $R^{3a}$, $R^4$ and $R^{4a}$ are each independently selected from the group consisting of H, $(C_1-C_6)$alkyl, benzyl and acetyl;
R, $R^a$ and $R^b$ are each independently selected from the group consisting of H, —OH, halo, —NH$_2$, azido, $(C_1-C_6)$ alkoxy$(C_1-C_6)$alkoxy and —W—$R^{30}$, wherein W is —O—C(O)— or —O—C(O)—NR$^{31}$—, $R^{31}$ is H and $R^{30}$ is $(C_1-C_6)$alkyl, —C(O)—$(C_1-C_4)$alkoxy-$(C_1-C_6)$alkyl, T, T-$(C_1-C_6)$alkyl, or T or T-$(C_1-C_6)$alkyl wherein T is substituted by one or two halo or $(C_1-C_6)$alkyl groups.
Preferred $R^{30}$ substituents are 2-fluorophenyl, 2,4-difluoro-phenyl, 2,6-dichlorophenyl, 2-methylphenyl, 2-thienylmethyl, 2-methoxy-carbonylethyl, thiazol-2-yl-methyl, 2-furyl, 2-methoxycarbonylbutyl and phenyl.

Preferred combinations of R, $R^a$ and $R^b$ include the following: 1) R, $R^a$ and $R^b$ are independently —OH or —O—C(O)—NH—$R^{30}$, especially wherein $R^a$ is —OH and R and $R^b$ are —O—C(O)—NH—$R^{30}$ and $R^{30}$ is selected from the preferred substituents identified above, or wherein R and $R^a$ are —OH and $R^b$ is —O—C(O)—NH—$R^{30}$ wherein $R^{30}$ is 2-fluorophenyl, 2,4-difluoro-phenyl, 2,6-dichlorophenyl; 2) $R^a$ is —OH, halogeno, azido or ($C_1$–$C_6$)-alkoxy($C_1$–$C_6$)alkoxy, $R^b$ is H, halogeno, azido or ($C_1$–$C_6$) alkoxy($C_1$–$C_6$)-alkoxy, and R is —O—C(O)—NH—$R^{30}$, especially compounds wherein $R^a$ is —OH, $R^b$ is H and $R^{30}$ is 2-fluorophenyl; 3) R, $R^a$ and $R^b$ are independently —OH or —O—C(O)—$R^{30}$ and $R^{30}$ is ($C_1$–$C_6$)alkyl, T, or T substituted by one or two halogeno or ($C_1$–$C_6$)alkyl groups, especially compounds wherein R is —OH and $R^a$ and $R^b$ are —O—C(O)—$R^{30}$ wherein $R^{30}$ is 2-furyl; and 4) R, $R^a$ and $R^b$ are independently —OH or halogeno. Three additional groups of preferred are compounds are those wherein the $C^{1'}$ anomeric oxy is beta, wherein the $C^{2'}$ anomeric oxy is beta, and wherein the R group is alpha.

$Ar^1$ is preferably phenyl or $R^{10}$-substituted phenyl, especially (4-$R^{10}$)-substituted phenyl. $R^{10}$ is preferably halo, more preferably fluoro.

$Ar^1$ can also be pyridyl, isoxazolyl, furanyl, pyrrolyl, thienyl, imidazolyl, pyrazolyl, thiazolyl, pyrazinyl, pyrimidinyl or pyridazinyl;

$Ar^2$ is preferably phenyl or $R^{11}$-phenyl, more preferably (4-$R^{11}$)-substituted phenyl.

$R^{11}$ is preferably lower alkoxy, especially methoxy, and halo, especially fluoro.

Preferably Q is a lower alkyl or a spiro group as defined above, wherein preferably $R^{13}$ and $R^{14}$ are each ethylene and $R^{12}$ is

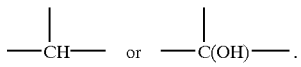

A preferred compound of formula I, therefore, is one in which $R^1$ is as defined above and in which the remaining variables have the following definitions:

$Ar^1$ is phenyl or $R^{10}$-substituted phenyl, wherein $R^{10}$ is halo;

$Ar^2$ is phenyl or $R^{11}$-phenyl, wherein $R^{11}$ is 1 to 3 substituents which are each independently selected from the group consisting of $C_1$–$C_6$ alkoxy and halo;

Q is a lower alkyl (i.e., C-1 to C-2) with Q=C-2 being preferred, or Q, with the 3-position ring carbon of the azetidinone, forms the group

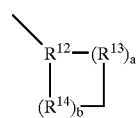

wherein preferably $R^{13}$ and $R^{14}$ are each ethylene and a and b are each 1, and wherein $R^{12}$ is

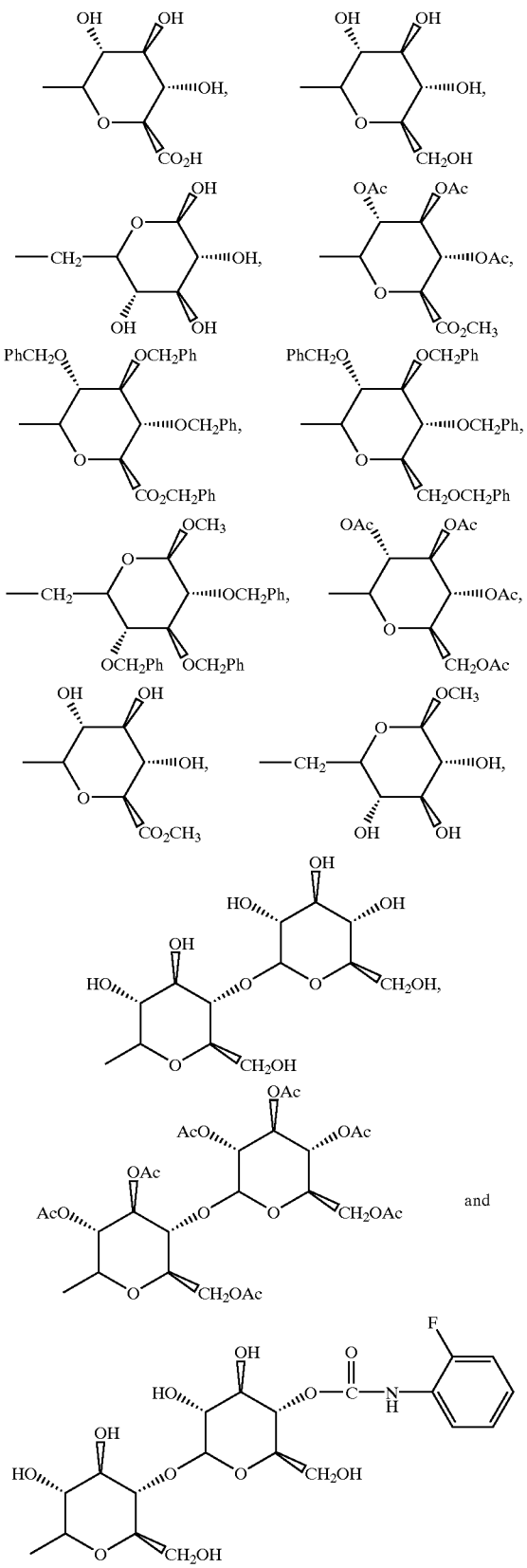

and

In another embodiment of the present invention, $R^1$ is preferably selected from the group consisting of:

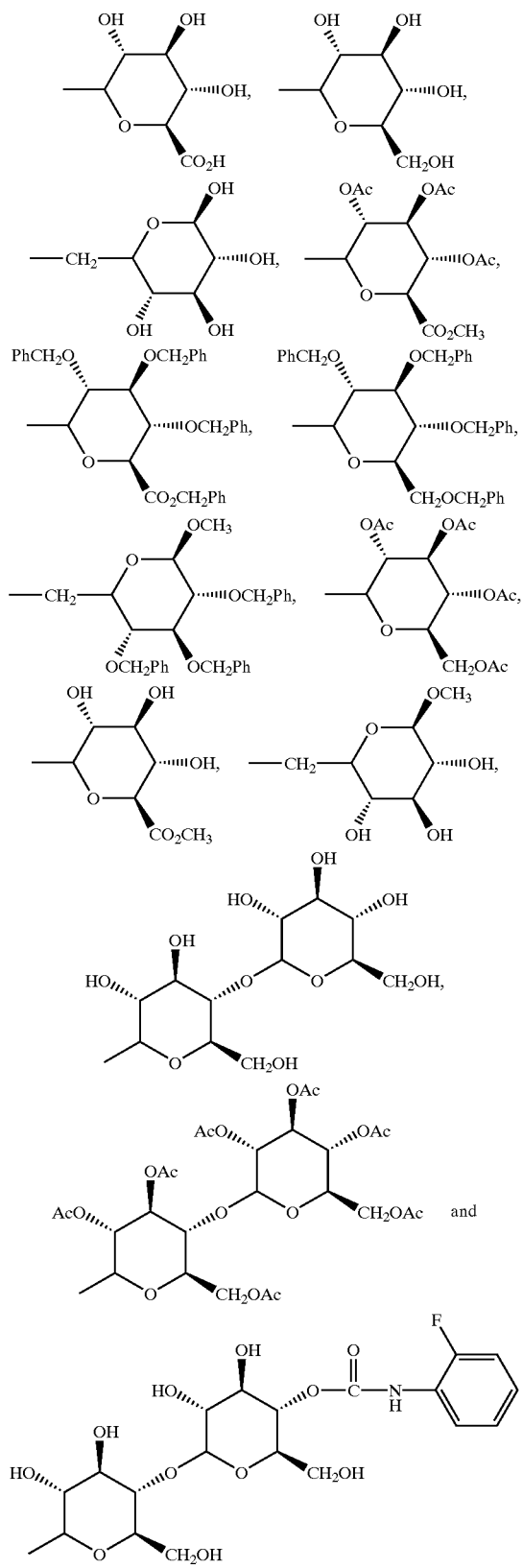

wherein Ac is acetyl and Ph is phenyl.

A preferred compound of the present invention is represented by the formula II.

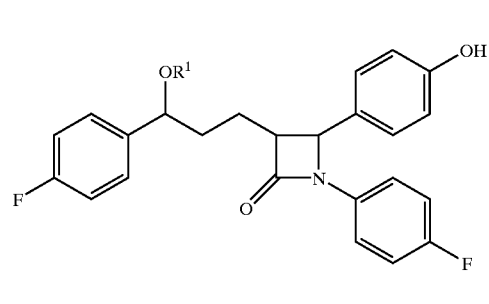

or a pharmaceutically acceptable salt or solvate thereof, wherein $R^1$ is defined as above.

A more preferred compound is one represented by formula III:

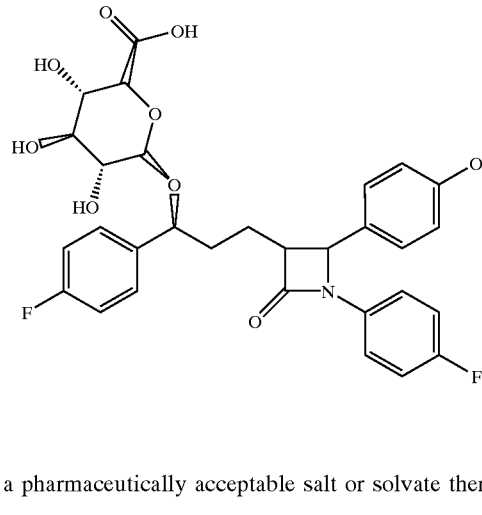

or a pharmaceutically acceptable salt or solvate thereof.

The compound of Formula III is a metabolite of ezetimibe (below):

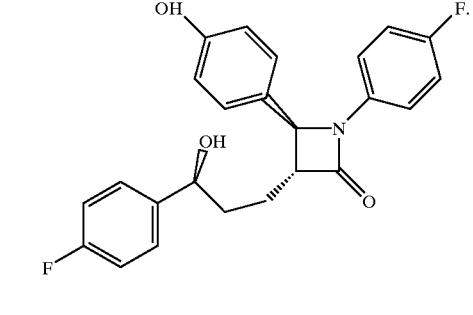

In another embodiment of the present invention, $R^1$ is $G^1$ and $R^{26}$ is $G^1$, wherein the $G^1$ moieties can be the same or different.

In another embodiment, the compound of Formula IA is represented by Formula IV:

IV

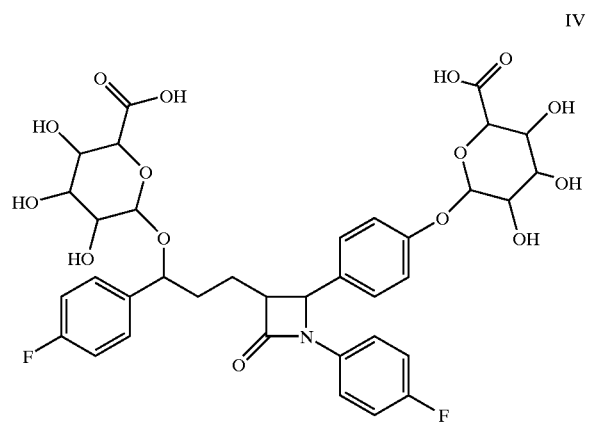

In another embodiment of the present invention, $R^1$ is $G^1$ in which $R^{33}$ is $(R^{35})(R^{36})$alkyl- wherein $R^{35}$ is $NH_2$ and $R^{36}$ is selected from the group consisting of: H, —$CH_3$, $CH_3CH_2$—, $CH_3CH_2CH_2$—, $(CH_3)_2CH$—, $(CH_3)_2CHCH_2$—, $CH_3CH_2(CH_3)CH$—, $CH_3CH_2(CH_3)CH$—, $HOOCCH_2CH_2$—, $HSCH_2$—, $HOOCCH_2$—, $(CH_3)SCH_2CH_2$—, $HOCH_2$—, $H_2N(CH_2)_4$—, $H_2NCH_2CHOH(CH_2)_2$—, $CH_3(OH)CH$—, $(NH_2)(NH)CNH(CH_2)_3$—, $H_2NC(O)CH_2$—, $HOOCCH(NH_3^+)CH_2SSCH_2$— and $H_2NCO(CH_2)_2$—.

In another embodiment of the present invention, $R^1$ is $G^1$ in which $R^{33}$ is

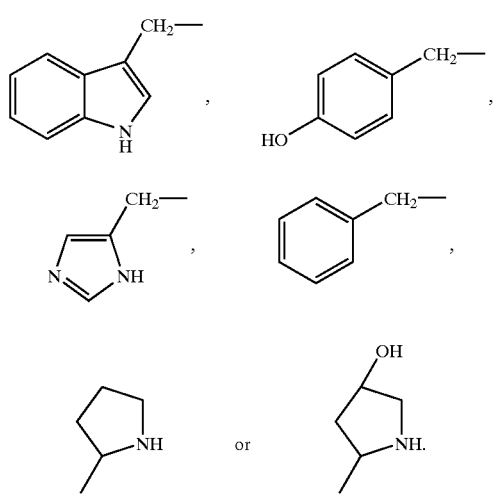

In another embodiment of the present invention, $R^1$ can be derived from an amino acid to yield, for example, the acyl functional group $G^1$ discussed above. "Amino acid" refers to natural and unnatural amino acids and includes but is not limited to Alanine, Arginine, Asparagine, Aspartic Acid, Cysteine, Glycine, Leucine, Serine and Valine.

In another embodiment of the present invention, $R^1$ can be $G^2$ which can be derived from an acetal, such as para-hexylbenzaldehyde diethyl acetal, citral diethyl acetal or cis-3-hexenyl acetal, in a manner well known to those skilled in the art.

Compounds of the invention have at least one asymmetrical carbon atom and therefore all isomers, including enantiomers, stereoisomers, rotamers, tautomers and racemates of the compounds of Formulae I and IA (where they exist) are contemplated as being part of this invention. The invention includes d and l stereoisomers in optically pure form and in admixture, including racemic mixtures. Isomers can be prepared using conventional techniques, either by reacting optically pure or optically enriched starting materials or by separating isomers of a compound of formula I. Isomers may also include geometric isomers, e.g., when a double bond is present.

Those skilled in the art will appreciate that for some of the compounds of the Formulae I and IA, one isomer will show greater pharmacological activity than other isomers.

Compounds of the invention with an amino group can form pharmaceutically acceptable salts with organic and inorganic acids. Examples of suitable organic and inorganic acids for salt formation are hydrochloric, sulfuric, phosphoric, acetic, citric, oxalic, malonic, salicylic, malic, fumaric, succinic, ascorbic, maleic, methanesulfonic and other organic and inorganic carboxylic acids well known to those in the art. The salt is prepared by contacting the free base form with a sufficient amount of the desired acid to produce a salt. The free base form may be regenerated by treating the salt with a suitable dilute aqueous base solution such as dilute aqueous sodium bicarbonate. The free base form differs from its respective salt form somewhat in certain physical properties, such as solubility in polar solvents, but the salt is otherwise equivalent to its respective free base forms for purposes of the invention.

Certain compounds of the invention are acidic (e.g., those compounds which possess a carboxyl group). These compounds form pharmaceutically acceptable salts with inorganic and organic bases. Examples of such salts are the sodium, potassium, calcium, aluminum, gold and silver salts. Also included are salts formed with pharmaceutically acceptable amines such as ammonia, alkyl amines, hydroxyalkylamines, N-methylglucamine and the like.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

Generally, compounds of formulae I or IA can be prepared by reacting, for example, a compound similar to that of formulae I or IA (in which $R^1$ is H) with a sugar or amino acid derivative, —$SO_3H$ or —$PO_3H$.

The 2-azetidinone portions of the compounds of formulae I and IA can be prepared by known methods, such as are disclosed in U.S. Pat. Nos. 5,631,365, 5,756,470, 5,767,115, 5,846,966, 6,207,822, U.S. Provisional Patent Application No. 60/279,288 filed Mar. 28, 2001, and PCT Patent Application WO 93/02048, each of which is incorporated herein by reference.

Sugars and amino acids and the derivatives thereof as defined by $R^1$ substituents defined above, are known in the art or are readily prepared by known methods.

For example, an azetidinone of Formula V, wherein $R^1$ is H, $Ar^1$, $Ar^2$ and $R^8$ are as defined above and Pr is a suitable hydroxy protecting group such as are described below, is reacted with one equivalent of a $G^a$-$OR^{30}$ (wherein $G^a$ is G, $G^1$ or $G^2$)

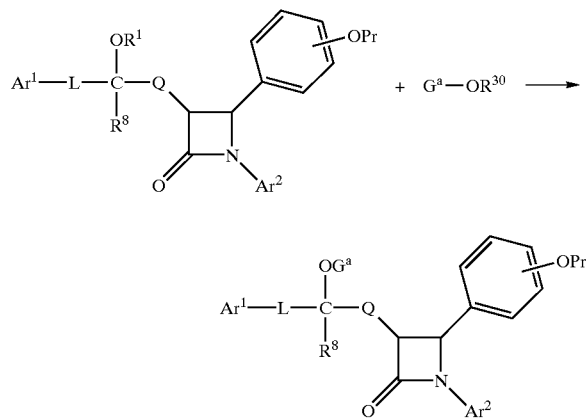

wherein $R^{30}$ is hydrogen or —CNHCCl$_3$ and the remaining variables are as defined above to obtain a compound of Formulae I or IA.

Preferably, the reactions described above involve a sugar derivative wherein the non-reactive hydroxy groups are protected by suitable protecting groups as defined above for $R^2$, $R^3$, $R^{3a}$, $R^4$, $R^{4a}$, $R^5$ and $R^7$ other than hydrogen, preferably lower alkyl, acetyl or benzyl, which groups can be removed after the reaction to provide the sugar conjugate. When the 1- and 4-position side chains of the 2-azetidinone include substituent groups which are reactive under the conditions used, said reactive groups are protected by suitable protecting groups prior to reaction with the sugar or the derivative thereof, and the protecting groups are subsequently removed. Depending on the nature of the protecting groups, the protecting groups on the sugar portion and on the 1- and 4-position side chains of the azetidinone can be removed sequentially or simultaneously.

M

Reactive groups not involved in the above processes can be protected during the reactions with conventional protecting groups which can be removed by standard procedures after the reaction. The following Table 1 shows some typical protecting groups:

TABLE 1

| Group to be Protected | Group to be Protected and Protecting Group |
|---|---|
| —COOH | —COOalkyl, —COObenzyl, —COOphenyl |
| >NH | >NCOalkyl, >NCObenzyl, >NCOphenyl, >NCH$_2$OCH$_2$CH$_2$Si(CH$_3$)$_3$, >NC(O)OC(CH$_3$)$_3$, >N-benzyl, >NSi(CH$_3$)$_3$, >NSi(CH$_3$)$_2$—C(CH$_3$)$_3$ |
| —NH$_2$ | (succinimide) |
| —OH | —OCH$_3$, —OCH$_2$OCH$_3$, —OSi(CH$_3$)$_3$, —OSi(CH$_3$)$_2$—C(CH$_3$)$_3$ or —OCH$_2$phenyl |

Alternatively, compounds of formulae I or IA can be prepared by incubating, for example, a compound similar to that of formulae I or IA (in which $R^1$ is H) (for example Compound 6A) with 9 recombinant cDNA expressed human UDP-Glucuronosyltransferases (UGT) SUPERSOMES® in the presence of Uridine 5'-diphosphate-glucuronic acid (UDPGA) as described in the Examples below.

In one embodiment of the present invention, the compositions can further comprise one or more pharmacological or therapeutic agents or drugs such as cholesterol biosynthesis inhibitors and/or therapeutic agents discussed below.

In another embodiment, the composition or treatment can further comprise one or more cholesterol biosynthesis inhibitors coadministered with or in combination with the compound(s) of Formulae I and/or IA discussed above.

Non-limiting examples of cholesterol biosynthesis inhibitors for use in the compositions and methods of the present invention include competitive inhibitors of HMG CoA reductase, the rate-limiting step in cholesterol biosynthesis, squalene synthase inhibitors, squalene epoxidase inhibitors and mixtures thereof. Non-limiting examples of suitable HMG CoA reductase inhibitors include statins such as lovastatin (for example MEVACOR® which is available from Merck & Co.), pravastatin (for example PRAVACHOL® which is available from Bristol Meyers Squibb), fluvastatin, simvastatin (for example ZOCOR® which is available from Merck & Co.), atorvastatin, cerivastatin, CI-981, ZD4522, rivastatin (sodium 7-(4-fluorophenyl)-2,6-diisopropyl-5-methoxymethylpyridin-3-yl)-3,5-dihydroxy-6-heptanoate), rosuvastatin, pitavastatin (such as NK-104 of Negma Kowa of Japan); HMG CoA synthetase inhibitors, for example L-659,699 ((E,E)-11-[3'R-(hydroxymethyl)-4'-oxo-2'R-oxetanyl]-3,5,7R-trimethyl-2,4-undecadienoic acid); squalene synthesis inhibitors, for example squalestatin 1; and squalene epoxidase inhibitors, for example, NB-598 ((E)-N-ethyl-N-(6,6-dimethyl-2-hepten-4-ynyl)-3-[(3,3'-bithiophen-5-yl)methoxy]benzenemethanamine hydrochloride) and other sterol biosynthesis inhibitors such as DMP-565. Preferred HMG CoA reductase inhibitors include lovastatin, pravastatin, fluvastatin, atorvastatin and simvastatin. The most preferred HMG CoA reductase inhibitor is simvastatin.

Generally, a total daily dosage of cholesterol biosynthesis inhibitor(s) can range from about 0.1 to about 160 mg per day, and preferably about 0.2 to about 80 mg/day in single or 2–3 divided doses.

In other alternative embodiments, the compositions or methods of the present invention can further comprise one or more peroxisome proliferator-activated receptor (PPAR) activators (such as fibrates), bile acid sequestrants (such as cholestyramine), ileal bile acid transport ("IBAT") inhibitors (such as benzothiepines) or apical sodium co-dependent bile acid transport ("ASBT") inhibitors, nicotinic acid (niacin) and/or derivatives (such as niceritrol, nicofuranose and acipimox), AcylCoA:Cholesterol O-acyltransferase ("ACAT") Inhibitors (such as avasimibe), Cholesteryl Ester Transfer Protein ("CETP") Inhibitors, probucol or derivatives, low-density lipoprotein (LDL) receptor activators, fish oil or Omega 3 fatty acids, natural water soluble fibers, such as psyllium, guar, oat and pectin, plant sterols, plant stanols and/or fatty acid esters of plant stanols, antioxidants, monocyte and macrophage inhibitors, hormone replacement agents such as androgens, estrogens, progestins, their pharmaceutically acceptable salts and derivatives, obesity control medications such as noradrenergic agents, serotonergic agents and thermogenic agents, blood modifiers which are chemically different from compounds I and IA (for example, they contain one or more different atoms, have a different arrangement of atoms or a different number of one or more atoms than compounds I and Ia) (such as anti-coagulants, antithrombotics and aspirin), cardiovascular agents which are chemically different from compounds I and IA (such as calcium channel blockers, angiotensin converting enzyme (ACE) inhibitors), antidiabetic medications (such as sulfonylureas (for example glimepiride or glipizide) and insulin) coadministered with or in combination with the compound(s) of Formulae I and/or IA discussed above.

Mixtures of any of the pharmacological or therapeutic agents described above can be used in the compositions of the present invention. Generally, a total daily dosage of the pharmacological or therapeutic agents described above can range from about 1 to about 5000 grams per day, and preferably about 1 to about 1000 grams per day in single or 2–4 divided doses.

Compared to the 2-azetidinone cholesterol lowering agents which are not sugar-substituted, the compounds of this invention have several pharmacological and physical advantages. The compounds are absorbed at a slower rate, give lower plasma levels and higher intestinal levels. Previous testing indicated the intestine as the likely site of activity of the 2-azetidinone compounds lacking a sugar substituent. See van Heek, M. et al, "In vivo mechanism-based discovery of a potent cholesterol absorption inhibitor (SCH 58235) through the identification of the active metabolites of SCH 48461," J. Pharmacol Exp. Ther., 283 (1997), pp. 157–163, and van Heek M. et al, "Comparison of the activity and deposition of the novel cholesterol absorption inhibitor, SCH 58235, and its glucuronide," Br. J. Pharmacol., 129, (2001) pp. 1748–1754. The instantly claimed compounds, which are excreted in the bile, provide efficient delivery of the compound to the desired site while minimizing systemic exposure, thereby decreasing potential toxicity problems.

In addition to the compound aspect, the present invention also relates to a method of lowering plasma cholesterol levels, which method comprises administering to a mammal in need of such treatment a hypocholesterolemic effective amount of a compound of formula I and/or IA of this invention. The compound is preferably administered in a pharmaceutically acceptable carrier suitable for oral, parental or transdermal administration.

The present invention also relates to a pharmaceutical composition comprising a compound of formula I and/or IA of this invention and a pharmaceutically acceptable carrier. The compounds of formula and/or IA can be administered in any conventional oral dosage form such as capsules, tablets, powders, cachets, suspensions or solutions. The formulations and pharmaceutical compositions can be prepared using conventional pharmaceutically acceptable excipients and additives and conventional techniques. Such pharmaceutically acceptable excipients and additives include non-toxic compatible fillers, binders, disintegrants, buffers, preservatives, anti-oxidants, lubricants, flavorings, thickeners, coloring agents, emulsifiers and the like.

The following formulation exemplifies a useful dosage form of this invention. In the formulation, the term "Active Compound" designates a compound of Formulae I or IA.

EXAMPLE

Tablets

| No. | Ingredient | mg/tablet |
|---|---|---|
| 1 | Active Compound | 10 |
| 2 | Lactose monohydrate NF | 55 |
| 3 | Microcrystalline cellulose NF | 20 |
| 4 | Povidone (K29-32) USP | 4 |
| 5 | Croscarmellose sodium NF | 8 |
| 6 | Sodium lauryl sulfate | 2 |
| 7 | Magnesium stearate NF | 1 |
| | Total | 100 |

Method of Manufacture

Mix Item No. 4 with purified water in suitable mixer to form binder solution Spray the binder solution and then water over Items 1, 2, 6 and a portion of Item 5 in a fluidized bed processor to granulate the ingredients. Continue fluidization to dry the damp granules. Screen the dried granules and blend with Item No. 3 and the remainder of Item 5. Add Item No. 7 and mix. Compress the mixture to appropriate size and weight on a suitable tablet machine.

The daily dose of a compound of formula I or IA is in the range of about 0.001 to about 1000 mg/kg of body weight per day, preferably about 30 mg/kg of body weight per day, and more preferably about 0.001 to about 1 mg/kg in single or divided doses. For an average body weight of 70 kg, the effective amount is therefore from about 0.1 to about 100 mg of drug per day, given in a single dose or 2–4 divided doses. The exact dose, however, is determined by the attending clinician and is dependent on the potency of the compound administered, the age, weight, condition and response of the patient.

For administration of pharmaceutically acceptable salts of the above compounds, the weights indicated above refer to the weight of the acid equivalent or the base equivalent of the therapeutic compound derived from the salt.

For the combinations of this invention wherein the substituted azetidinone is administered in combination with a cholesterol biosynthesis inhibitor, the typical daily dose of the cholesterol biosynthesis inhibitor is 0.1 to 80 mg/kg of mammalian weight per day administered in single or divided dosages, usually once or twice a day: for example, for HMG CoA reductase inhibitors, about 10 to about 40 mg per dose is given 1 to 2 times a day, giving a total daily dose of about 10 to 80 mg per day, and for the other cholesterol biosynthesis inhibitors, about 1 to 1000 mg per dose is given 1 to 2 times a day, giving a total daily dose of about 1 mg to about 2 g per day. The exact dose of any component of the combination to be administered is determined by the attending clinician and is dependent on the potency of the compound administered, the age, weight, condition and response of the patient.

Where the components of a combination are administered separately, the number of doses of each component given per day may not necessarily be the same, e.g. where one component may have a greater duration of activity, and will therefore need to be administered less frequently.

Since the present invention relates to the reduction of plasma cholesterol levels by treatment with a combination of active ingredients wherein said active ingredients may be administered separately, the invention also relates to combining separate pharmaceutical compositions in kit form. That is, a kit is contemplated wherein two separate units are combined: a cholesterol biosynthesis inhibitor pharmaceutical composition and a sugar-substituted 2-azetidinone absorption inhibitor pharmaceutical composition. The kit will preferably include directions for the administration of the separate components. The kit form is particularly advantageous when the separate components must be administered in different dosage forms (e.g. oral and parenteral) or are administered at different dosage intervals.

The compounds of Formulae I and IA and the treatment compositions of the present invention can inhibit the intestinal absorption of cholesterol in mammals and can be useful in the treatment and/or prevention of conditions, for example vascular conditions, such as atherosclerosis, hypercholesterolemia and sitosterolemia, stroke, obesity and lowering of plasma levels of cholesterol in mammals, in particular in humans.

In another embodiment of the present invention, the compositions and therapeutic combinations of the present invention can inhibit sterol absorption (as a sterol absorption inhibitor) or reduce plasma concentration of at least one sterol selected from the group consisting of phytosterols (such as sitosterol, campesterol, stigmasterol and avenosterol), 5α-stanols (such as cholestanol, 5α-campestanol, 5α-sitostanol), cholesterol and mixtures thereof. The plasma concentration can be reduced by administering to a mammal in need of such treatment an effective amount of at least one treatment composition comprising at least one compound of Formulae I and/or IA described above. The reduction in plasma concentration of sterols can range from about 1 to about 70 percent, and preferably about 10 to about 50 percent. Methods of measuring serum total blood cholesterol and total LDL cholesterol are well known to those skilled in the art and for example include those disclosed in PCT WO 99/38498 at page 11, incorporated by reference herein. Methods of determining levels of other sterols in serum are disclosed in H. Gylling et al., "Serum Sterols During Stanol Ester Feeding in a Mildly Hypercholesterolemic Population", J. Lipid Res. 40: 593–600 (1999), incorporated by reference herein.

We have found that the compounds of this invention lower plasma lipid levels and hepatic cholesterol ester levels. Compounds of this invention have been found to inhibit the intestinal absorption of cholesterol and to significantly reduce the formation of liver cholesteryl esters in animal models. Thus, compounds of this invention are hypocholesterolemic agents by virtue of their ability to inhibit the esterification and/or intestinal absorption of cholesterol; they are therefore useful in the treatment and prevention of atherosclerosis in mammals, in particular in humans.

Compounds 6A and Example 1 below disclosed in U.S. Pat. Nos. 5,767,115 and 5,756,470 respectively, demonstrate pharmacological activity as hypocholesterolemic agents.

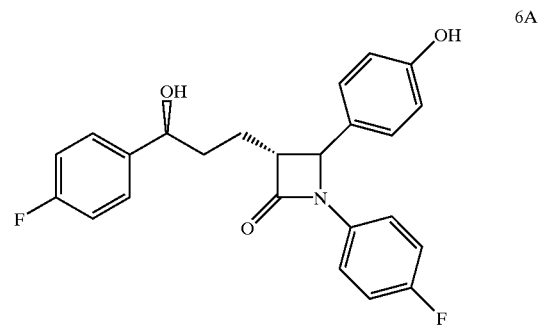

6A

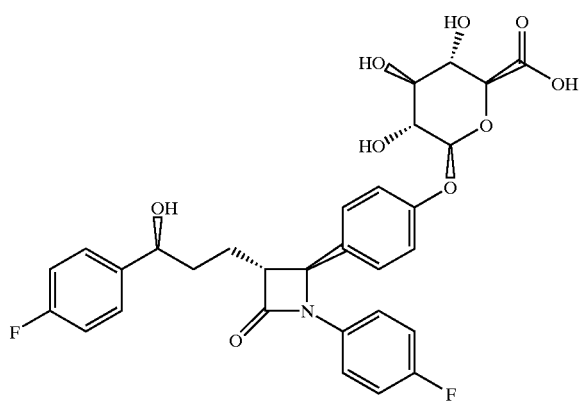

EXAMPLE 1

The in vivo activity (see Table 1 below) of the compounds 6A and Example 1 above, can be determined by the following procedure.

In Vivo Assay of Hypolipidemic Agents Using the Hyperlipidemic Hamster

Hamsters are separated into groups of six and given a controlled cholesterol diet (Purina Chow #5001 containing 0.5% cholesterol) for seven days. Diet consumption is monitored to determine dietary cholesterol exposure in the presence of test compounds. The animals are dosed with the test compound once daily beginning with the initiation of diet. Dosing is by oral gavage of 0.2 mL of corn oil alone (control group) or solution (or suspension) of test compound in corn oil. All animals moribund or in poor physical condition are euthanized. After seven days, the animals are anesthetized by IM injection of ketamine and sacrificed by decapitation. Blood is collected into Vacutainer™ tubes containing EDTA for plasma total cholesterol and triglyceride analysis and the liver excised for free and esterified cholesterol and triglyceride tissue analysis. Data is reported as percent reduction of plasma cholesterol and hepatic cholesterol esters versus control levels.

Data is reported as percent change (i.e., percent reduction in plasma cholesterol and in hepatic cholesterol esters) versus control, therefore, negative numbers indicate a positive cholesterol-lowering effect. The assay results are shown in Table 1 below.

TABLE 1

| | % Reduction in Plasma Cholesterol | % Reduction in Cholesterol Esters | Dose mg/kg |
|---|---|---|---|
| Example 1 | −58 | −95 | 3 |
| 6A | −59 | −95 | 1 |

Experiment 3 described below demonstrates that both the compound of formula III and Example 1 yield Compound 6A (all shown herein above) following hydrolysis with β-glucuronidase.

Experiment Nos. 1 and 2 confirm that Compound 6A yields both Example 1 and the compound of formula III following incubations of Compound 6A with GI tract microsomes or 9 recombinant cDNA expressed human UDP-Glucuronosyltransferases such as UGT2B7 SUPERSOMES®.

Since both Compound 6A and Example 1 are shown to demonstrate pharmacological activity (Table 1), the compounds of formulas I, IA, II and III of the present invention are expected to exert similar pharmacological activity.

Experimental

1. Incubations of Compound 6A with pooled human liver microsomes (n=10) supplemented with Uridine 5'-diphosphate-glucuronic acid (UDPGA) yielded one Compound 6A-glucuronide (retention time 7 min) consistent with Example 1 (phenolic glucuronide). However, incubations of Compound 6A with pooled (n=4) and two individuals human jejunum microsomes supplemented with UDPGA yielded two distinct Compound 6A-glucuronides (retention times ~7 and ~9 min) consistent with Example 1 (phenolic) and Compound III (benzylic) glucuronides, respectively. LC/MS analysis showed that both peaks have m/z 584.

2. Compound 6A was incubated with commercially available 9 recombinant cDNA expressed human UDP-Glucuronosyltransferases (UGT SUPERSOMES®. which are available from B. D. Gentest of Woburn, Mass.) in the presence of UDPGA (TABLE 2). SUPERSOMES® UGT1A1 and UGT1A3 yielded exclusively Example 1. Incubations with UGT2B7 SUPERSOMES® yielded mainly Compound III accompanied by a small amount of Example 1.

TABLE 2

Screening of UGT isozymes and Formation of Compound 6A-Glucuronides with 100 μM Compound 6A

| Human UGT SUPERSOMES ® + UDPGA | % Conversion to Example 1 | % Conversion to Compound III |
|---|---|---|
| UGT1A1 | 79.50 | 0 |
| UGT1A3 | 73.40 | 0 |
| UGT1A4 | 0 | 0.78 |
| UGT1A6 | 0 | 0 |
| UGT1A7 | 0 | 0 |
| UGT1A9 | 0.30 | 0.50 |
| UGT1A10 | 0 | 0 |
| UGT2B7 | 0.50 | 6.16 |
| UGT2B15 | 6.06 | 0 |
| Insect control | 0 | 0 |

3. β-Glucuronidase hydrolysis of the mixture of Example 1 and Compound III (Compound 6A-benzylic glucuronides) obtained from jejunum microsomes (5, 10, 20, 30 and 180 min, TABLE 3) demonstrates that Example 1 was hydrolyzed at a faster rate than Compound III. After hydrolyzing for 18 h, both peaks were hydrolyzed to form a single Compound 6A peak.

TABLE 3
Hydrolysis with β-Glucuronidase after 2 hr Incubation of Human Jejunum Microsomes with 50 μM Compound 6A Supplemented with UDPGA
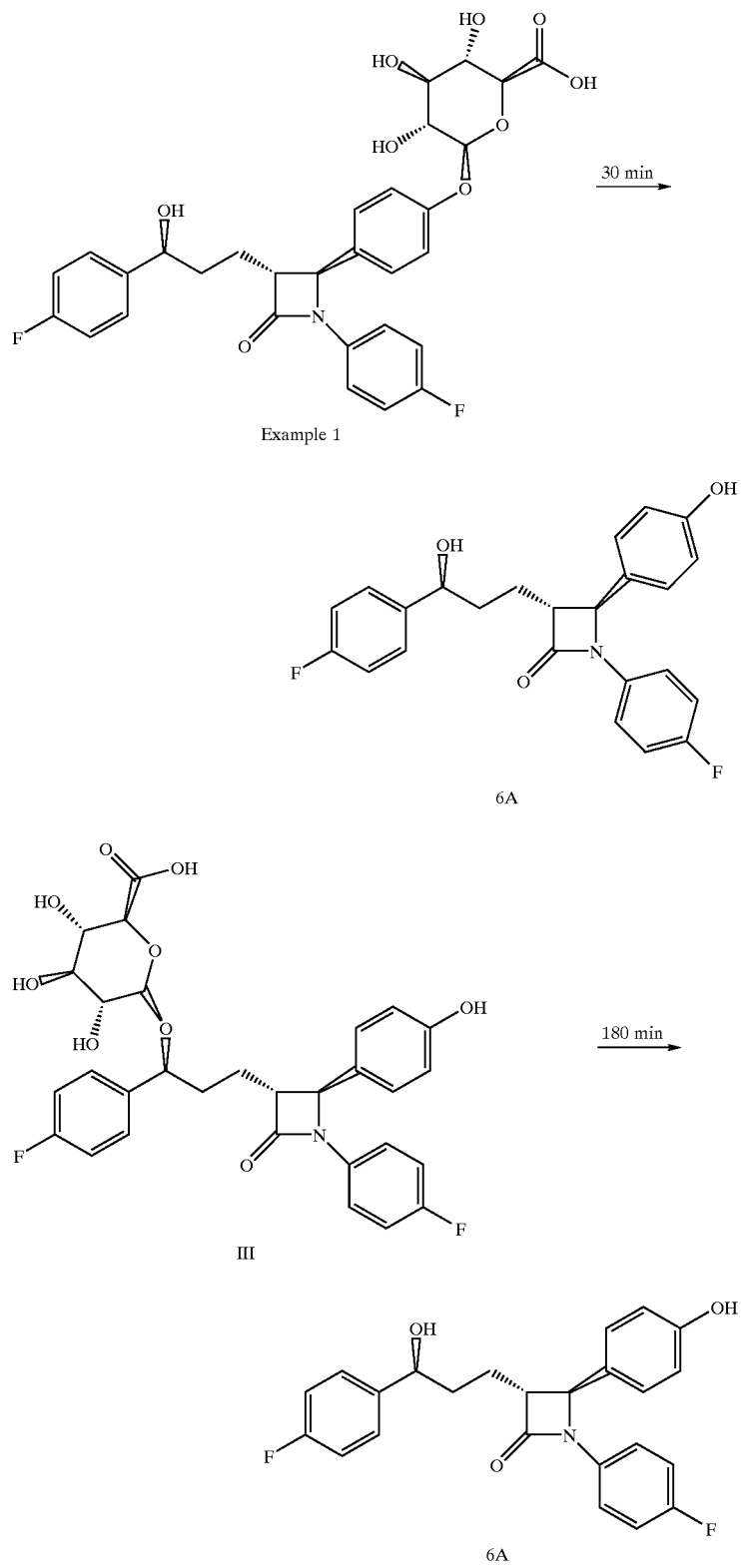

TABLE 3-continued

Hydrolysis with β-Glucuronidase after 2 hr Incubation of
Human Jejunum Microsomes with 50 μM Compound 6A
Supplemented with UDPGA

| Hydrolysis time | % of Example 1 (Phenolic Glucuronide) | % of Compound III (Benzylic Glucuronide) | % of Compound 6A |
|---|---|---|---|
| No hydrolysis | 31.68 | 32.14 | 32.06 |
| 5 min | 2.23 | 19.30 | 68.10 |
| 10 min | 1.04 | 18.58 | 61.88 |
| 20 min | 0.77 | 15.12 | 66.02 |
| 30 min | 0 | 11.22 | 80.14 |
| 180 min | 0 | 6.5 | 84.67 |
| Control: 180 min, No microsomes, No UDPGA | — | — | 72.92 |

Scale Up Production and Structure Identification of Compound III

Scale-up Preparation and Extraction of Compound III

Scale up production of Compound III was performed using 1.23 mg (0.05 mM) of $^{14}$C-SCH 58235 and 60 mg protein of cDNA expressed recombinant human UGT2B7 SUPERSOMES® supplemented with UDPGA (2 mM) in 60 ml Tris buffer, pH 7.4. The incubation was carried out for 2 hr at 37° C. and subjected to solid phase extraction (SPE). The methanol elution from SPE was dried and Compound III was further purified as described below.

Isolation of Compound III for LC/NMR Analysis

Compound III was isolated using preparative HPLC with fraction collection. The dried residue from SPE methanol elution was reconstituted in ca. 3 mL of CH$_3$OH and centrifuged (16,000 g) to remove solid precipitate. Methanol was evaporated and the residue redissolved in ca. 2 mL of CH$_3$OH:DMSO (20:80, v:v). The preparative HPLC column (Inertsil C8, 250×20 mm) provided a retention time of ca. 15.0 and 20.6 min for Example 1 and Compound III, respectively. Compound III was isolated using 200 μL injections (10 in total) onto the preparative column collecting 0.5 min fractions. Compound III eluted in fractions numbered 37 (18.5 min) through 44 (22.0 min) for each injection. These fractions were within the observed retention time for the Compound III were analyzed by LC-MS/MS. The fractions (18.5–22 min) were combined and dried.

Determination of Structure of Compound III by LC/NMR

LC-NMR was carried out using mobile phases of 20 mM ammonium acetate-d$_3$ (pH 7.0) and acetonitrile. The HPLC gradient was 30% acetonitrile for 10 minutes, and then went up to 40% for 20 minutes. The metabolite eluted at approximately 10 minute. LC-NMR was conducted in stop-flow mode on the metabolite peak apex. 1D proton and 2D proton-proton correlation spectra were recorded on Varian 600 MHz NMR spectrometer at 20° C. Corresponding NMR data were obtained on synthetic standards Compound 6A and Example 1 (Compound 6A-phenolic glucuronide). Based on the NMR data of the sample and the comparison with those from the standards, the proton assignments for this metabolite (MW 585) were made. The structure of this metabolite was identified to be Compound 6A-benzylic-glucuronide (Compound III).

It will be appreciated by those skilled in the art that changes could be made to the embodiments described above without departing from the broad inventive concept thereof. It is understood, therefore, that this invention is not limited to the particular embodiments disclosed, but it is intended to cover modifications which are within the spirit and scope of the invention, as defined by the appended claims.

Therefore, we claim:

1. A compound represented by the Formula (IA):

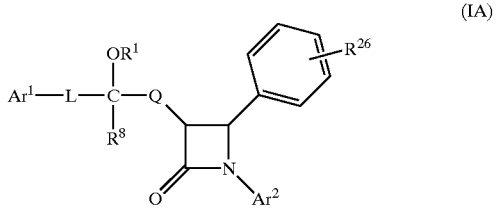

(IA)

or a pharmaceutically acceptable salt or solvate thereof, wherein in Formula (IA):

R$^1$ is selected from the group consisting of H, G, G$^1$, G$^2$, —SO$_3$H and —PO$_3$H;

G is selected from the group consisting of: H,

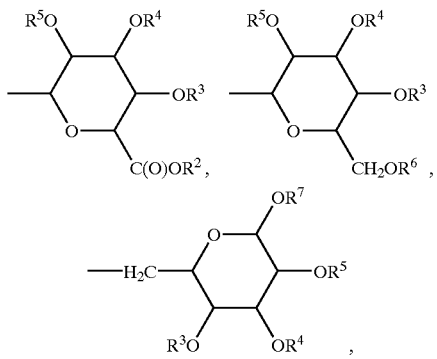

-continued

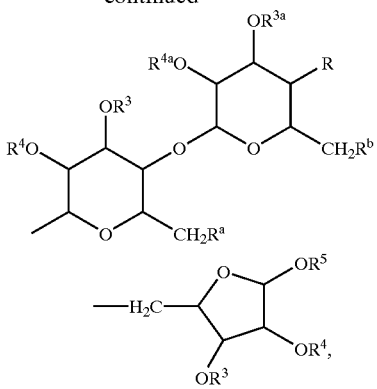

and wherein R, $R^a$ and $R^b$ are each independently selected from the group consisting of H, —OH, halo, —NH$_2$, azido, (C$_1$–C$_6$)alkoxy(C$_1$–C$_6$)alkoxy or —W—R$^{30}$;

W is independently selected from the group consisting of —NH—C(O)—, —O—C(O)—, —O—C(O)—N(R$^{31}$)—, —NH—C(O)—N(R$^{31}$)— and —O—C(S)—N(R$^{31}$)—;

$R^2$ and $R^6$ are each independently selected from the group consisting of H, (C$_1$–C$_6$)alkyl, acetyl, aryl and aryl(C$_1$–C$_6$)alkyl;

$R^3$, $R^4$, $R^5$, $R^7$, $R^{3a}$ and $R^{4a}$ are each independently selected from the group consisting of H, (C$_1$–C$_6$)alkyl, acetyl, aryl(C$_1$–C$_6$)alkyl, —C(O)(C$_1$–C$_6$)alkyl and —C(O)aryl;

$R^{30}$ is independently selected from the group consisting of $R^{32}$-substituted T, $R^{32}$-substituted-T-(C$_1$–C$_6$)alkyl, $R^{32}$-substituted-(C$_2$–C$_4$)alkenyl, $R^{32}$-substituted-(C$_1$–C$_6$)alkyl, $R^{32}$-substituted-(C$_3$–C7)cycloalkyl and $R^{32}$-substituted-(C$_3$–C7)cycloalkyl(C$_1$–C$_6$)alkyl;

$R^{31}$ is independently selected from the group consisting of H and (C$_1$–C$_4$)alkyl;

T is independently selected from the group consisting of phenyl, furyl, thienyl, pyrrolyl, oxazolyl, isoxazolyl, thiazolyl, isothiazolyl, benzothiazolyl, thiadiazolyl, pyrazolyl, imidazolyl and pyridyl;

$R^{32}$ is independently selected from 1–3 substituents which are each independently selected from the group consisting of H, halo, (C$_1$–C$_4$)alkyl, —OH, phenoxy, —CF$_3$, —NO$_2$, (C$_1$–C$_4$)alkoxy, methylenedioxy, oxo, (C$_1$–C$_4$)alkylsulfanyl, (C$_1$–C$_4$)alkylsulfinyl, (C$_1$–C$_4$)alkylsulfonyl, —N(CH$_3$)$_2$, —C(O)—NH(C$_1$–C$_4$)alkyl, —C(O)—N((C$_1$–C$_4$)alkyl)$_2$, —C(O)—(C$_1$–C$_4$)alkyl, —C(O)—(C$_1$–C$_4$)alkoxy and pyrrolidinylcarbonyl; or $R^{32}$ is a covalent bond and $R^{31}$, the nitrogen to which it is attached and $R^{32}$ form a pyrrolidinyl, piperidinyl, N-methyl-piperazinyl, indolinyl or morpholinyl group, or a (C$_1$–C$_4$)alkoxycarbonyl-substituted pyrrolidinyl, piperidinyl, N-methylpiperazinyl, indolinyl or morpholinyl group;

$G^1$ is represented by the structure:

wherein $R^{33}$ is independently selected from the group consisting of $R^{34}$-substituted alkyl, (R$^{35}$)(R$^{36}$)alkyl-,

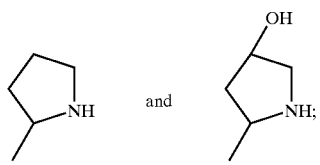

$R^{34}$ is one to three substituents, each $R^{34}$ being independently selected from the group consisting of HOOC—, HS—, (CH$_3$)S—, H$_2$N—, (NH$_2$)(NH)C(NH)—, (NH$_2$)C(O)—, HOOCCH(NH$_3^+$)CH$_2$SS—;

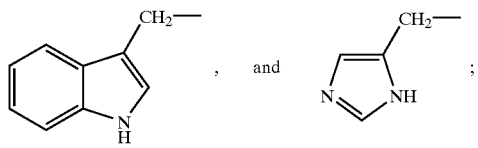

$R^{35}$ is independently selected from the group consisting of H and NH$_2$—;

$R^{36}$ is independently selected from the group consisting of H, unsubstituted alkyl, $R^{34}$-substituted alkyl, unsubstituted cycloalkyl, $R^{34}$-substituted cycloalkyl, HOOCCH$_2$CH$_2$—, HSCH$_2$—, HOOCCH$_2$—, (CH$_3$)SCH$_2$CH$_2$—, HOCH$_2$—, H$_2$N(CH$_2$)$_4$—, H$_2$NCH$_2$CHOH(CH$_2$)$_2$—, CH$_3$(OH)CH—, (NH$_2$)(NH)CNH(CH$_2$)$_3$—, H$_2$NC(O)CH$_2$—, HOOCCH(NH$_3^+$)CH$_2$SSCH$_2$— and H$_2$NCO(CH$_2$)$_2$— wherein when $R^{35}$ is H, $R^{36}$ is not H or unsubstituted alkyl;

$G^2$ is represented by the structure:

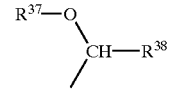

wherein $R^{37}$ and $R^{38}$ are each independently selected from the group consisting of (C$_1$–C$_6$)alkyl and aryl;

$R^{26}$ is one to five substituents, each $R^{26}$ being independently selected from the group consisting of:
a) H;
b) —OH;
c) —OCH$_3$;
d) fluorine;
e) chlorine;
f) —O-G;
g) —O-G$^1$;
h) —O-G$^2$;
i) —SO$_3$H; and
j) —PO$_3$H;

provided that when $R^1$ is H, $R^{26}$ is not H, —OH, —OCH$_3$ or —O-G;

Ar$^1$ is aryl, $R^{10}$-substituted aryl, heteroaryl or $R^{10}$-substituted heteroaryl;

Ar$^2$ is aryl, $R^{11}$-substituted aryl, heteroaryl or $R^{11}$-substituted heteroaryl;

L is selected from the group consisting of:
a) a covalent bond;
b) —(CH$_2$)$_q$—, wherein q is 1–6;
c) —(CH$_2$)$_e$-E-(CH$_2$)$_r$—, wherein E is —O—, —C(O)—, phenylene, —NR$^{22}$— or
d) —S(O)$_{0-2}$—, e is 0–5 and r is 0–5, provided that the sum of e and r is 1–6;
e) —(C$_2$–C$_6$)alkenylene-;

f) —(CH$_2$)$_f$—V—(CH$_2$)$_g$—, wherein V is C$_3$–C$_6$cycloalkylene, f is 1–5 and g) g is 0–5, provided that the sum of f and g is 1–6; and h)

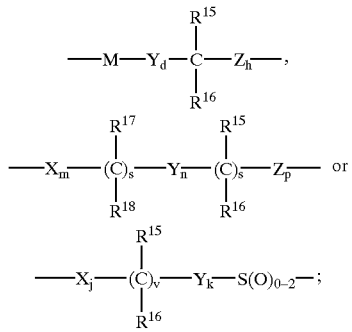

wherein M is —O—, —S—, —S(O)— or —S(O)$_2$—;

X, Y and Z are each independently selected from the group consisting of —CH$_2$—, —CH(C$_1$–C$_6$)alkyl- and —C(di-(C$_1$–C$_6$)alkyl)-;

R$^8$ is selected from the group consisting of H and alkyl;

R$^{10}$ and R$^{11}$ are each independently selected from the group consisting of 1–3 substituents which are each independently selected from the group consisting of (C$_1$–C$_6$)alkyl, —OR$^{19}$, —O(CO)R$^{19}$, —O(CO)OR$^{21}$, —O(CH$_2$)$_{1-5}$OR$^{19}$, —O(CO)NR$^{19}$R$^{20}$, —NR$^{19}$R$^{20}$, —NR$^{19}$(CO)R$^{20}$, —NR$^{19}$(CO)OR$^{21}$, —NR$^{19}$(CO)NR$^{20}$R$^{25}$, —NR$^{19}$SO$_2$R$^{21}$, —COOR$^{19}$, —CONR$^{19}$R$^{20}$, —COR$^{19}$, —SO$_2$NR$^{19}$R$^{20}$, S(O)$_{0-2}$R$^{21}$, —O(CH$_2$)$_{1-10}$—COOR$^{19}$, —O(CH$_2$)$_{1-10}$CONR$^{19}$R$^{20}$, —(C$_1$–C$_6$ alkylene)—COOR$^{19}$, —CH=CH—COOR$^{19}$, —CF$_3$, —CN, —NO$_2$ and halo;

R$^{15}$ and R$^{17}$ are each independently selected from the group consisting of —OR$^{19}$, —OC(O)R$^{19}$, —OC(O)OR$^{21}$, —OC(O)NR$^{19}$R$^{20}$;

R$^{16}$ and R$^{18}$ are each independently selected from the group consisting of H, (C$_1$–C$_6$)alkyl and aryl;

or R$^{15}$ and R$^{16}$ together are =O, or R$^{17}$ and R$^{18}$ together are =O;

d is 1, 2 or 3;

h is 0, 1, 2, 3 or 4;

s is 0 or 1;

t is 0 or 1;

m, n and p are each independently selected from 0–4;

provided that at least one of s and t is 1, and the sum of m, n, p, s and t is 1–6; provided that when p is 0 and t is 1, the sum of m, n and p is 1–5; and provided that when p is 0 and s is 1, the sum of m, t and n is 1–5;

v is 0 or 1;

j and k are each independently 1–5, provided that the sum of j, k and v is 1–5;

Q is a bond, —(CH$_2$)$_q$—, wherein q is 1–6, or, with the 3-position ring carbon of the azetidinone, forms the spiro group

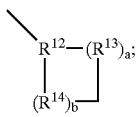

wherein R$^{12}$ is

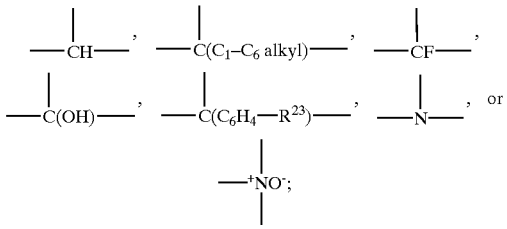

R$^{13}$ and R$^{14}$ are each independently selected from the group consisting of —CH$_2$—, —CH(C$_1$–C$_6$ alkyl)-, —C(di-(C$_1$–C$_6$) alkyl), —CH=CH— and —C(C$_1$–C$_6$ alkyl)=CH—; or R$^{12}$ together with an adjacent R$^{13}$, or R$^{12}$ together with an adjacent R$^{14}$, form a —CH=CH— or a —CH=C(C$_1$–C$_6$ alkyl)- group;

a and b are each independently 0, 1, 2 or 3, provided both are not zero; provided that when R$^{13}$ is —CH=CH— or —C(C$_1$–C$_6$ alkyl)=CH—, a is 1; provided that when R$^{14}$ is —CH=CH— or —C(C$_1$–C$_6$ alkyl)=CH—, b is 1; provided that when a is 2 or 3, the R$^{13}$'s can be the same or different; and provided that when b is 2 or 3, the R$^{14}$'s can be the same or different;

and when Q is a bond and L is

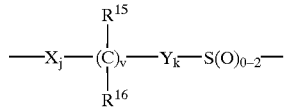

then Ar$^1$ can also be pyridyl, isoxazolyl, furanyl, pyrrolyl, thienyl, imidazolyl, pyrazolyl, thiazolyl, pyrazinyl, pyrimidinyl or pyridazinyl;

R$^{19}$ and R$^{20}$ are each independently selected from the group consisting of H, (C$_1$–C$_6$)alkyl, aryl and aryl-substituted (C$_1$–C$_6$)alkyl;

R$^{21}$ is (C$_1$–C$_6$)alkyl, aryl or R$^{24}$-substituted aryl;

R$^{22}$ is H, (C$_1$–C$_6$)alkyl, aryl (C$_1$–C$_6$)alkyl, —C(O)R$^{19}$ or —COOR$^{19}$;

R$^{23}$ and R$^{24}$ are each independently selected from the group consisting of 1–3 substituents which are each independently selected from the group consisting of H, (C$_1$–C$_6$)alkyl, (C$_1$–C$_6$)alkoxy, —COOH, NO$_2$, —NR$^{19}$R$^{20}$, —OH and halo; and R$^{25}$ is H, —OH or (C$_1$–C$_6$)alkoxy.

2. The compound according to claim 1, wherein R$^1$ is G.

3. The compound according to claim 2, wherein G is selected from the group consisting of

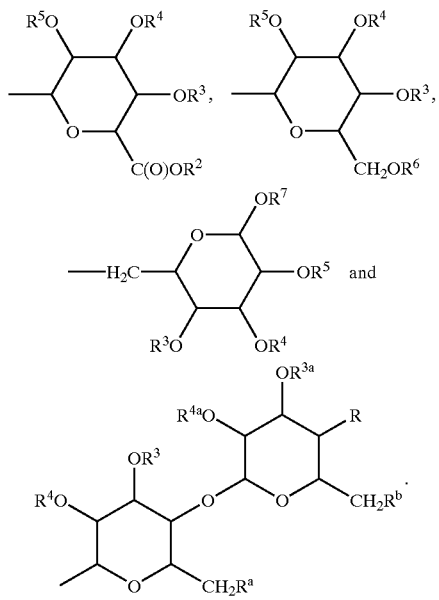

4. The compound according to claim 3, wherein G is selected from the group consisting of 5. The compound according to claim 4, wherein G is selected from the group consisting of:

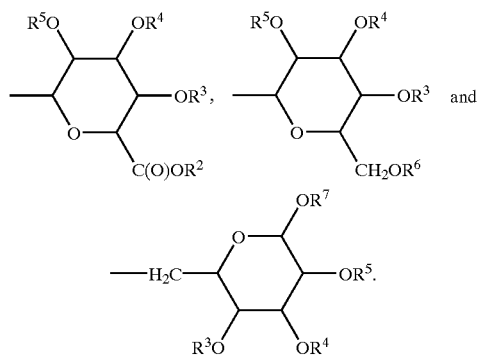

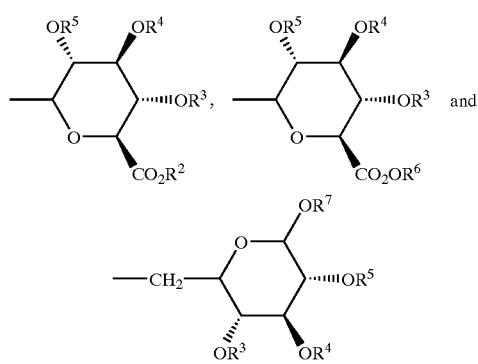

wherein:
R$^2$, R$^3$, R$^4$, R$^5$, R$^6$ and R$^7$ are each independently selected from the group consisting of H, (C$_1$–C$_6$)alkyl, benzyl and acetyl.

6. The compound according to claim 5, wherein G is:

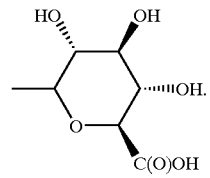

7. The compound according to claim 3, wherein G is:

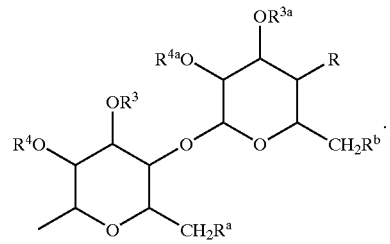

8. The compound according to claim 7, wherein G is:

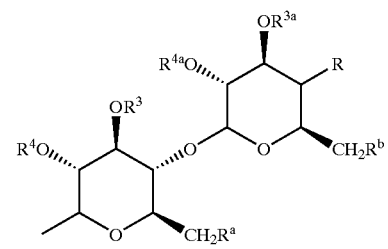

wherein:
R$^3$, R$^{3a}$, R$^4$ and R$^{4a}$ are selected from the group consisting of H, (C$_1$–C$_6$)alkyl, benzyl and acetyl;
R, R$^a$ and R$^b$ are independently selected from the group consisting of H, —OH, halogeno, —NH$_2$, azido, (C$_1$–C$_6$)alkoxy(C$_1$–C$_6$)alkoxy and —W—R$^{30}$, wherein W is —O—C(O)— or —O—C(O)—NR$^{31}$—, R$^{31}$ is H and R$^{30}$ is (C$_1$–C$_6$)alkyl, —C(O)—(C$_1$–C$_4$)alkoxy-(C$_1$–C$_6$)alkyl, T, T-(C$_1$–C$_6$)alkyl, or T or T-(C$_1$–C$_6$) alkyl wherein T is substituted by one or two halogeno or (C$_1$–C$_6$)alkyl groups.

9. The compound according to claim 8, wherein R$^{30}$ is 2-fluorophenyl, 2,4-difluorophenyl, 2-methylphenyl, 2-thienylmethyl, 2-methoxycarbonyl-ethyl, thiazol-2-yl-methyl, 2-methoxycarbonylbutyl or phenyl, or W is —O—C(O)— and R$^{30}$ is (C$_1$–C$_6$)alkyl, T, or T substituted by one or two halo or (C$_1$–C$_6$)alkyl groups.

10. The compound according to claim 1, wherein R$^1$ is G$^1$ which is represented by the structure:

wherein R$^{33}$ is (R$^{35}$)(R$^{36}$)HC—, wherein R$^{35}$ is NH$_2$ and R$^{36}$ is selected from the group consisting of:
H, —CH$_3$, CH$_3$CH$_2$—, CH$_3$CH$_2$CH$_2$—, (CH$_3$)$_2$CH—, (CH$_3$)$_2$CHCH$_2$—, CH$_3$CH$_2$(CH$_3$)CH—, CH$_3$CH$_2$(CH$_3$)CH—, HOOCCH$_2$CH$_2$—, HSCH$_2$—, HOOCCH$_2$—, (CH$_3$)SCH$_2$CH$_2$—, HOCH$_2$—, H$_2$N(CH$_2$)$_4$—, H$_2$NCH$_2$CHOH(CH$_2$)$_2$—, CH$_3$(OH)CH—, (NH$_2$)(NH)CNH(CH$_2$)$_3$—, H$_2$NC(O)CH$_2$—, HOOCCH(NH$_3{}^+$)CH$_2$SSCH$_2$—, H$_2$NCO(CH$_2$)$_2$—.

11. The compound according to claim 1, wherein Ar$^1$ is phenyl or R$^{10}$-substituted phenyl and Ar$^2$ is phenyl or R$^{11}$-substituted phenyl.

12. The compound according to claim 11, wherein R$^{10}$ is halo and R$^{11}$ is lower alkoxy or halo.

13. The compound according to claim 1, wherein:

Ar$^1$ is phenyl or R$^{10}$-substituted phenyl;
Ar$^2$ is phenyl or R$^{11}$-phenyl;
R$^{10}$ is halo;
R$^{11}$ is lower alkoxy or halo;
Q is —(CH$_2$)$_q$—, wherein q is 2–6; or Q, with the 3-position ring carbon of the azetidinone, forms the group

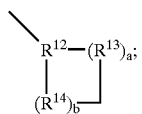

wherein R$^{13}$ and R$^{14}$ are each ethylene and a and b are each 1, and wherein R$^{12}$ is

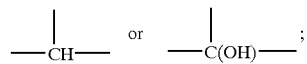

R$^1$ is selected from the group consisting of

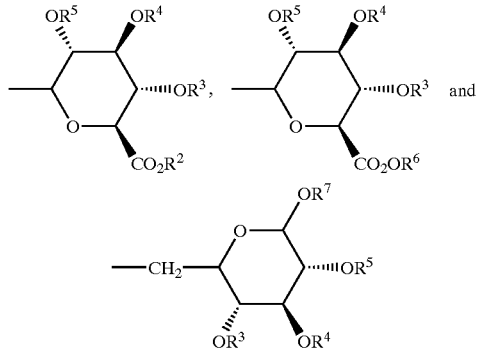

wherein R$^2$, R$^3$, R$^4$, R$^5$, R$^6$ and R$^7$ are each independently selected from the group consisting of H, (C$_1$–C$_6$)alkyl, benzyl and acetyl; or R$^1$ is

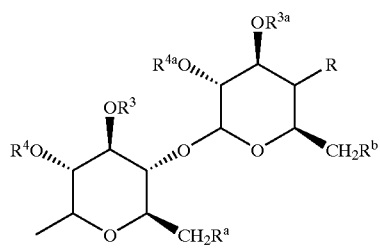

wherein R$^3$, R$^{3a}$, R$^4$ and R$^{4a}$ are each independently selected from the group consisting of H, (C$_1$–C$_6$)alkyl, benzyl and acetyl; and R, R$^a$ and R$^b$ are each independently selected from the group consisting of H, —OH, halo, —NH$_2$, azido, (C$_1$–C$_6$)alkoxy(C$_1$–C$_6$)alkoxy and —W—R$^{30}$, wherein W is —O—C(O)— or —O—C(O)—NR$^{31}$—, R$^{31}$ is H and R$^{30}$ is (C$_1$–C$_6$)alkyl, —C(O)—(C$_1$–C$_4$)alkoxy-(C$_1$–C$_6$)alkyl, T, T-(C$_1$–C$_6$)alkyl, or T or T-(C$_1$–C$_6$)alkyl wherein T is substituted by one or two halo or (C$_1$–C$_6$)alkyl groups.

14. A compound represented by the Formula II:

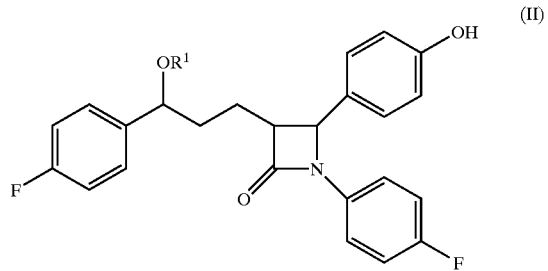

or a pharmaceutically acceptable salt or solvate thereof, wherein in Formula II:

R$^1$ is selected from the group consisting of G, G$^1$, G$^2$, —SO$_3$H and —PO$_3$H, G is selected from the group consisting of:

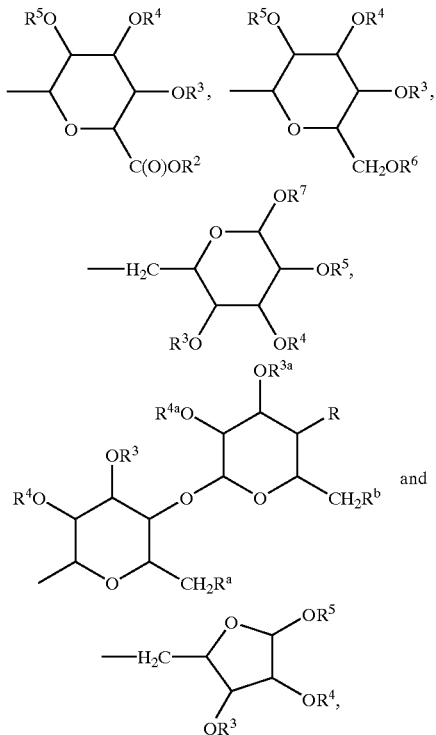

wherein R, R$^a$ and R$^b$ are each independently selected from the group consisting of H, —OH, halo, —NH$_2$, azido, (C$_1$–C$_6$)alkoxy(C$_1$–C$_6$)alkoxy or —W—R$^{30}$;

W is independently selected from the group consisting of —NH—C(O)—, —O—C(O)—, —O—C(O)—N(R$^{31}$)—, —NH—C(O)—N(R$^{31}$)— and —O—C(S)—N(R$^{31}$)—;

R$^2$ and R$^6$ are each independently selected from the group consisting of H, (C$_1$–C$_6$)alkyl, acetyl, aryl and aryl(C$_1$–C$_6$)alkyl;

R$^3$, R$^4$, R$^5$, R$^7$, R$^{3a}$ and R$^{4a}$ are each independently selected from the group consisting of H, (C$_1$–C$_6$) alkyl, acetyl, aryl(C$_1$–C$_6$)alkyl, —C(O)(C$_1$–C$_6$)alkyl and —C(O)aryl;

R$^{30}$ is independently selected from the group consisting of R$^{32}$-substituted T, R$^{32}$-substituted-T-(C$_1$–C$_6$)

alkyl, $R^{32}$-substituted-$(C_2-C_4)$alkenyl, $R^{32}$-substituted-$(C_1-C_6)$alkyl, $R^{32}$-substituted-$(C_3-C_7)$cycloalkyl and $R^{32}$-substituted-$(C_3-C_7)$cycloalkyl $(C_1-C_6)$alkyl;

$R^{31}$ is independently selected from the group consisting of H and $(C_1-C_4)$alkyl;

T is independently selected from the group consisting of phenyl, furyl, thienyl, pyrrolyl, oxazolyl, isoxazolyl, thiazolyl, isothiazolyl, benzothiazolyl, thiadiazolyl, pyrazolyl, imidazolyl and pyridyl;

$R^{32}$ is independently selected from 1–3 substituents which are each independently selected from the group consisting of H, halo, $(C_1-C_4)$alkyl, —OH, phenoxy, —$CF_3$, —$NO_2$, $(C_1-C_4)$alkoxy, methylenedioxy, oxo, $(C_1-C_4)$alkylsulfanyl, $(C_1-C_4)$alkylsulfinyl, $(C_1-C_4)$alkylsulfonyl, —$N(CH_3)_2$, —C(O)—NH$(C_1-C_4)$alkyl, —C(O)—N$((C_1-C_4)$alkyl$)_2$, —C(O)—$(C_1-C_4)$alkyl, —C(O)—$(C_1-C_4)$alkoxy and pyrrolidinylcarbonyl; or $R^{32}$ is a covalent bond and $R^{31}$, the nitrogen to which it is attached and $R^{32}$ form a pyrrolidinyl, piperidinyl, N-methyl-piperazinyl, indolinyl or morpholinyl group, or a $(C_1-C_4)$alkoxycarbonyl-substituted pyrrolidinyl, piperidinyl, N-methylpiperazinyl, indolinyl or morpholinyl group;

$G^1$ is represented by the structure:

wherein $R^{33}$ is independently selected from the group consisting of $R^{34}$-substituted alkyl, $(R^{35})(R^{36})$alkyl-,

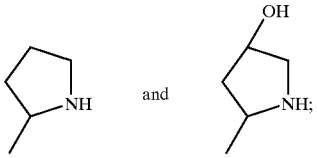

$R^{34}$ is one to three substituents, each $R^{34}$ being independently selected from the group consisting of HOOC—, HS—, $(CH_3)$S—, $H_2$N—, $(NH_2)(NH)$C(NH)—, $(NH_2)$C(O)—, and HOOCCH$(NH_3^+)$CH$_2$SS—

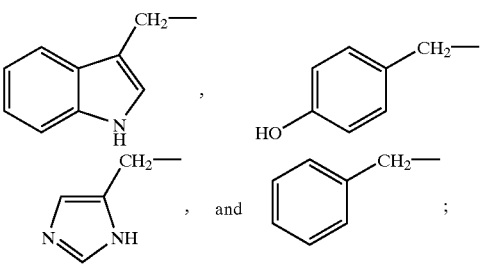

$R^{35}$ is independently selected from the group consisting of H and $NH_2$—;

$R^{36}$ is independently selected from the group consisting of H, unsubstituted alkyl, $R^{34}$-substituted alkyl, unsubstituted cycloalkyl, $R^{34}$-substituted cycloalkyl, HOOCCH$_2$CH$_2$—, HSCH$_2$—, HOOCCH$_2$—, $(CH_3)$SCH$_2$CH$_2$—, HOCH$_2$—, $H_2$N(CH$_2$)$_4$—, $H_2$NCH$_2$CHOH(CH$_2$)$_2$—, $CH_3$(OH)CH—, (NH$_2$)(NH)CNH(CH$_2$)$_3$—, $H_2$NC(O)CH$_2$—, HOOCCH(NH$_3^+$)CH$_2$SSCH$_2$— and $H_2$NCO(CH$_2$)$_2$— wherein when $R^{35}$ is H, $R^{36}$ is not H or unsubstituted alkykl;

$G^2$ is represented by the structure:

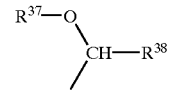

wherein $R^{37}$ and $R^{38}$ are each independently selected from the group consisting of $(C_1-C_6)$alkyl and aryl.

15. A compound represented by the Formula III:

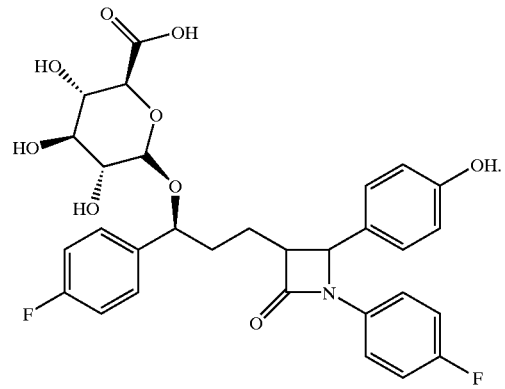

16. A compound represented by the structural formula I

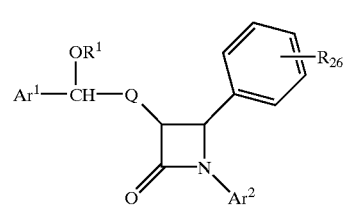

or a pharmaceutically acceptable salt or solvate thereof, wherein $R^{26}$ is selected from the group consisting of:

a) OH;
b) OCH$_3$;
c) fluorine and
d) chlorine, provided that when $R^1$ is H, $R^{26}$ is not —OH, $R^1$ is selected from the group consisting of

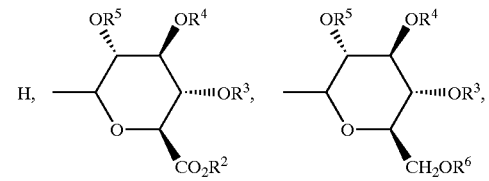

-continued

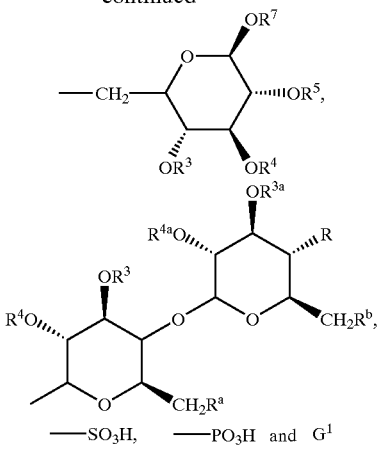

wherein G¹ is represented by the structure:

wherein $R^{33}$ is independently selected from the group consisting of $R^{34}$-substituted alkyl, $(R^{35})(R^{36})$alkyl-,

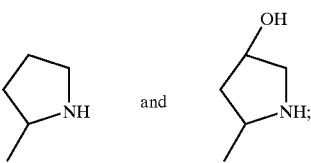

$R^{34}$ is one to three substituents, each $R^{34}$ being independently selected from the group consisting of HOOC—, HS—, $(CH_3)S$—, $H_2N$—, $(NH_2)(NH)C(NH)$—, $(NH_2)C(O)$—, $HOOCCH(NH_3^+)CH_2SS$—

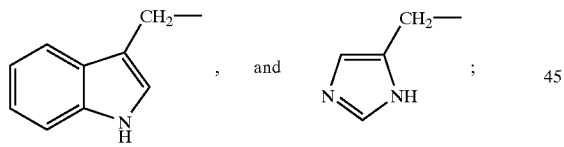

$R^{35}$ is independently selected from the group consisting of H and $NH_2$—;
$R^{36}$ is independently selected from the group consisting of H, unsubstituted alkyl, $R^{34}$-substituted alkyl, unsubstituted cycloalkyl, $R^{34}$-substituted cycloalkyl, $HOOCCH_2CH_2$—, $HSCH_2$—, $HOOCCH_2$—, $(CH_3)SCH_2CH_2$—, $HOCH_2$—, $H_2NC(CH_2)_4$—, $H_2NCH_2CHOH(CH_2)_2$—, $CH_3(OH)CH$—, $(NH_2)(NH)CNH(CH_2)_3$—, $H_2NC(O)CH_2$—, $HOOCCH(NH_3^+)CH_2SSCH_2$— and $H_2NCO(CH_2)_2$— wherein when $R^{35}$ is H, $R^{36}$ is not H or unsubstituted alkykl;
R, $R^a$ and $R^b$ are each independently selected from the group consisting of H, —OH, halogeno, —$NH_2$, azido, $(C_1-C_6)$alkoxy$(C_1-C_6)$-alkoxy or —W—$R^{30}$;
W is independently selected from the group consisting of —NH—C(O)—, —O—C(O)—, —O—C(O)—N$(R^{31})$—, —NH—C(O)—N$(R^{31})$— and —O—C(S)—N$(R^{31})$—;

$R^2$ and $R^6$ are each independently selected from the group consisting of H, $(C_1-C_6)$alkyl, aryl and aryl$(C_1-C_6)$ alkyl;
$R^3$, $R^4$, $R^5$, $R^7$, $R^{3a}$ and $R^{4a}$ are each independently selected from the group consisting of H, $(C_1-C_6)$alkyl, aryl$(C_1-C_6)$alkyl, —C(O)$(C_1-C_6)$alkyl and —C(O) aryl;
$R^{30}$ is independently selected form the group consisting of $R^{32}$-substituted T, $R^{32}$-substituted-T-$(C_1-C_6)$alkyl, $R^{32}$-substituted-$(C_2-C_4)$alkenyl, $R^{32}$-substituted-$(C_1-C_6)$alkyl, $R^{32}$-substituted-$(C_3-C7)$cycloalkyl and $R^{32}$-substituted-$(C_3-C7)$cycloalkyl$(C_1-C_6)$alkyl;
$R^{31}$ is independently selected from the group consisting of H and $(C_1-C_4)$alkyl;
T is independently selected from the group consisting of phenyl, furyl, thienyl, pyrrolyl, oxazolyl, isoxazolyl, thiazolyl, isothiazolyl, benzothiazolyl, thiadiazolyl, pyrazolyl, imidazolyl and pyridyl;
$R^{32}$ is independently selected from 1–3 substituents which are each independently selected from the group consisting of H, halogeno, $(C_1-C_4)$alkyl, —OH, phenoxy, —$CF_3$, —$NO_2$, $(C_1-C_4)$alkoxy, methylenedioxy, oxo, $(C_1-C_4)$alkylsulfanyl, $(C_1-C_4)$alkylsulfinyl, $(C_1-C_4)$alkylsulfonyl, —$N(CH_3)_2$, —C(O)—NH$(C_1-C_4)$alkyl, —C(O)—N$((C_1-C_4)$alkyl$)_2$, —C(O)—$(C_1-C_4)$alkyl, —C(O)—$(C_1-C_4)$alkoxy and pyrrolidinylcarbonyl; or $R^{32}$ is a covalent bond and $R^{31}$, the nitrogen to which it is attached and $R^{32}$ form a pyrrolidinyl, piperidinyl, N-methylpiperazinyl, indolinyl or morpholinyl group, or a $(C_1-C_4)$alkoxycarbonyl-substituted pyrrolidinyl, piperidinyl, N-methylpiperazinyl, indolinyl or morpholinyl group;
$Ar^1$ is aryl, $R^{10}$-substituted aryl, heteroaryl, $R^{10}$-substituted heteroaryl;
$Ar^2$ is aryl, $R^{11}$-substituted aryl, heteroaryl, $R^{11}$-substituted heteroaryl;
Q is —$(CH_2)_q$—, wherein q is 2–6, or, with the 3-position ring carbon of the azetidinone, forms the spiro group

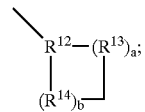

$R^{12}$ is

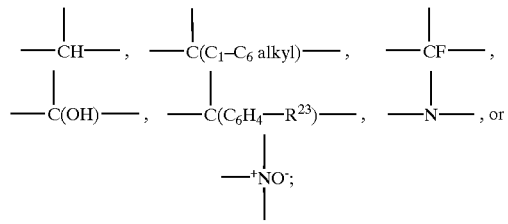

$R^{13}$ and $R^{14}$ are each independently selected from the group consisting of —$CH_2$—, —CH$(C_1-C_6$ alkyl)-, —C(di-$(C_1-C_6)$ alkyl), —CH=CH— and —C$(C_1-C_6$ alkyl)=CH—; or $R^{12}$ together with an adjacent $R^{13}$, or $R^{12}$ together with an adjacent $R^{14}$, form a —CH=CH— or a —CH=C$(C_1-C_6$ alkyl)- group;
a and b are each independently 0, 1, 2 or 3, provided both are not zero; provided that when $R^{13}$ is —CH=CH— or —C($C_1$-$C_6$ alkyl)=CH—, a is 1; provided that when $R^{14}$ is —CH=CH— or —C($C_1$-$C_6$ alkyl)=CH—, b is 1; provided that when a is 2 or 3, the $R^{13}$'s can be the same or different; and provided that when b is 2 or 3, the $R^{14}$'s can be the same or different;

$R^{10}$ and $R^{11}$ are each independently selected from the group consisting of 1–3 substituents independently selected from the group consisting of ($C_1$-$C_6$)alkyl, —$OR^{19}$, —O(CO)$R^{19}$, —O(CO)$OR^{21}$, —O($CH_2$)$_{1-5}$$OR^{19}$, —O(CO)$NR^{19}R^{20}$, —$NR^{19}R^{20}$, —$NR^{19}$(CO)$R^{20}$, —$NR^{19}$(CO)$OR^{21}$, —$NR^{19}$(CO)$NR^{20}R^{25}$, —$NR^{19}SO_2R^{21}$, —$COOR^{19}$, —$CONR^{19}R^{20}$, —$COR^{19}$, —$SO_2NR^{19}R^{20}$, $S(O)_{0-2}R^{21}$, —O($CH_2$)$_{1-10}$—$COOR^{19}$, —O($CH_2$)$_{1-10}$$CONR^{19}R^{20}$, —($C_1$-$C_6$ alkylene)-$COOR^{19}$, —CH=CH—$COOR^{19}$, —$CF_3$, —CN, —$NO_2$ and halogen;

$R^{19}$ and $R^{20}$ are each independently selected from the group consisting of H, ($C_1$-$C_6$)alkyl, aryl and aryl-substituted ($C_1$-$C_6$)alkyl;

$R^{21}$ is ($C_1$-$C_6$)alkyl, aryl or $R^{24}$-substituted aryl;

$R^{22}$ is H, ($C_1$-$C_6$)alkyl, aryl ($C_1$-$C_6$)alkyl, —C(O)$R^{19}$ or —$COOR^{19}$;

$R^{23}$ and $R^{24}$ are each independently 1–3 groups which are each independently selected from the group consisting of H, ($C_1$-$C_6$)alkyl, ($C_1$-$C_6$)alkoxy, —COOH, $NO_2$, —$NR^{19}R^{20}$, —OH and halo; and $R^{25}$ is H, —OH or ($C_1$-$C_6$)alkoxy.

17. A pharmaceutical composition for the treatment of atherosclerosis, hypercholesterolemia, sitosterolemia, diabetes, obesity or lowering concentration of a sterol in plasma of a mammal, comprising an effective amount of a compound of claim 1 in a pharmaceutically acceptable carrier.

18. A pharmaceutical composition comprising a cholesterol-lowering effective amount of a compound of claim 1 in a pharmaceutically acceptable carrier.

19. A pharmaceutical composition for the treatment of atherosclerosis, hypercholesterolemia, sitosterolemia, diabetes, obesity or lowering concentration of a sterol in plasma of a mammal, comprising an effective amount of a combination of a compound of claim 1, a cholesterol biosynthesis inhibitor and a pharmaceutically acceptable carrier.

20. The pharmaceutical composition according to claim 19, wherein the cholesterol biosynthesis inhibitor is selected from the group consisting of lovastatin, pravastatin, fluvastatin, simvastatin, atorvastatin, ((E,E)-11-[3'R-(hydroxy-methyl)-4'-oxo-2'R-oxetanyl]-3,5,7R-trimethyl-2,4-undecadienoic acid), squalestatin 1, ((E)-N-ethyl-N-(6,6-dimethyl-2-hepten-4-ynyl)-3-[(3,3'-bithiophen-5-yl)methoxy]benzene-methanamine hydrochloride), pitavastatin and rosuvastatin.

21. The pharmaceutical composition according to claim 20, wherein the cholesterol biosynthesis inhibitor is simvastatin.

22. A kit comprising in separate containers in a single package pharmaceutical compositions for use in combination to treat atherosclerosis, hypercholesterolemia, sitosterolemia, diabetes, obesity or lowering concentration of a sterol in plasma of a mammal which comprises in one container an effective amount of a cholesterol biosynthesis inhibitor in a pharmaceutically acceptable carrier, and in a second container, an effective amount of a compound of claim 1 in a pharmaceutically acceptable carrier.

23. A pharmaceutical composition comprising a cholesterol-lowering effective amount of the compound of claim 15 and a pharmaceutically acceptable carrier.

24. A pharmaceutical composition for the treatment of atherosclerosis, or for the reduction of cholesterol levels, comprising an effective amount of a combination of the compound of claim 15, a cholesterol biosynthesis inhibitor and a pharmaceutically acceptable carrier.

25. The pharmaceutical composition according to claim 24, wherein the cholesterol biosynthesis inhibitor is selected from the group consisting of lovastatin, pravastatin, fluvastatin, simvastatin, atorvastatin, ((E,E)-11-[3'R-(hydroxy-methyl)-4'-oxo-2'R-oxetanyl]-3,5,7R-trimethyl-2,4-undecadienoic acid), squalestatin 1, ((E)-N-ethyl-N-(6,6-dimethyl-2-hepten-4-ynyl)-3-[(3,3'-bithiophen-5-yl)methoxy]benzene-methanamine hydrochloride), pitavastatin and rosuvastatin.

26. The pharmaceutical composition according to claim 25, wherein the cholesterol biosynthesis inhibitor is simvastatin.

27. A kit comprising in separate containers in a single package pharmaceutical compositions for use in combination to treat atherosclerosis or to reduce cholesterol levels which comprises in one container an effective amount of a cholesterol biosynthesis inhibitor in a pharmaceutically acceptable carrier, and in a second container, an effective amount of the compound of claim 15 in a pharmaceutically acceptable carrier.

* * * * *

UNITED STATES PATENT AND TRADEMARK OFFICE
CERTIFICATE OF CORRECTION

PATENT NO. : 6,982,251 B2 Page 1 of 1
APPLICATION NO. : 10/166942
DATED : January 3, 2006
INVENTOR(S) : Ghosal et al.

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by (205) days Delete the phrase "by 205" and insert -- by 142 days --

Signed and Sealed this

Twenty-eighth Day of November, 2006

JON W. DUDAS
*Director of the United States Patent and Trademark Office*